(12) United States Patent
Greaves et al.

(10) Patent No.: US 7,303,589 B2
(45) Date of Patent: *Dec. 4, 2007

(54) PROCESS FOR DYEING HUMAN KERATIN FIBERS, HAVING A LIGHTENING EFFECT, COMPRISING AT LEAST ONE FLUORESCENT COMPOUND AND COMPOSITIONS OF THE SAME

(75) Inventors: Andrew Greaves, Montevrain (FR); Nicolas Daubresse, la Celles St Cloud (FR); Xavier Radisson, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/814,336

(22) Filed: Apr. 1, 2004

(65) Prior Publication Data
US 2005/0011018 A1 Jan. 20, 2005

Related U.S. Application Data

(60) Provisional application No. 60/468,103, filed on May 6, 2003.

(30) Foreign Application Priority Data

Apr. 1, 2003 (FR) .................................. 03 04022

(51) Int. Cl.
A61K 7/13 (2006.01)
(52) U.S. Cl. ...................... 8/405; 8/406; 8/407; 8/410; 8/411; 8/421; 8/646; 132/202; 132/208
(58) Field of Classification Search ................ 8/405, 8/406, 407, 410, 411, 421, 646; 132/202, 132/208
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Ditmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. ............... 96/101 |
| 3,658,985 A | 4/1972 | Olson, Jr. et al. |
| 3,856,550 A | 12/1974 | Bens et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Vanlerberghe et al. |

(Continued)

FOREIGN PATENT DOCUMENTS

AT 302 534 10/1972

(Continued)

OTHER PUBLICATIONS

STIC Search Report U.S. Appl. No. 10/814,338.*

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure relates to a process for dyeing human keratin materials having a lightening effect, applying to the materials a composition comprising, in a cosmetically acceptable medium, at least one fluorescent dye having the following formula:

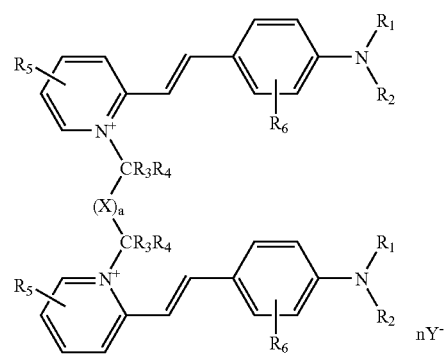

Figure 1:
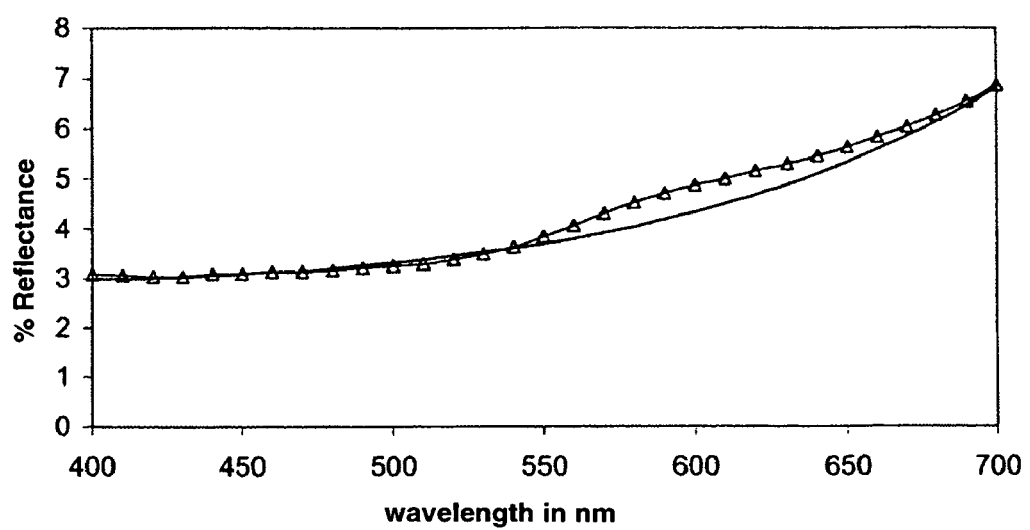

The present disclosure also relates to at least one fluorescent dye, to a composition comprising the at least one fluorescent dye, and to a multi-compartment kit comprising the said composition.

97 Claims, 1 Drawing Sheet

U.S. PATENT DOCUMENTS

| | | | |
|---|---|---|---|
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,237,243 A | 12/1980 | Quack et al. |
| 4,240,450 A | 12/1980 | Grollier et al. |
| 4,256,458 A * | 3/1981 | Degen et al. ............... 8/506 |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |
| 4,591,160 A | 5/1986 | Grollier |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Hanazawa et al. |
| 5,089,252 A | 2/1992 | Grollier et al. |
| 5,139,037 A | 8/1992 | Grollier et al. |
| 5,188,639 A | 2/1993 | Schultz et al. |
| 5,196,189 A | 3/1993 | Jacquet et al. |
| 5,275,808 A | 1/1994 | De Groot et al. |
| 5,356,438 A | 10/1994 | Kim et al. |
| 5,445,655 A | 8/1995 | Kuhn et al. |
| 5,635,461 A | 6/1997 | Onitsuka et al. |
| 5,708,151 A | 1/1998 | Möckli |
| 5,733,343 A | 3/1998 | Mockli |
| 5,744,127 A | 4/1998 | Giuseppe et al. |
| 5,792,221 A | 8/1998 | Lagrange et al. |
| 5,830,446 A | 11/1998 | Berthiaume et al. |
| 5,833,997 A | 11/1998 | Mahieu et al. |
| 5,853,708 A | 12/1998 | Cauwet et al. |
| 5,873,494 A | 2/1999 | Dallas, Jr. |
| 5,958,392 A | 9/1999 | Grollier et al. |
| 5,962,522 A | 10/1999 | Wacher et al. |
| 6,001,135 A | 12/1999 | Rondeau et al. |
| 6,106,577 A | 8/2000 | Audousset et al. |
| 6,120,780 A | 9/2000 | Dupuis et al. |
| 6,180,666 B1 | 1/2001 | Wacher et al. |
| 6,260,556 B1 | 7/2001 | Legrand et al. |
| 6,375,958 B1 | 4/2002 | Cauwet et al. |
| 6,391,062 B1 | 5/2002 | Vandenbossche et al. |
| 6,436,151 B2 | 8/2002 | Cottard et al. |
| 6,436,153 B2 | 8/2002 | Rondeau |
| 6,475,248 B2 | 11/2002 | Ohashi et al. |
| 6,570,019 B2 | 5/2003 | Braun et al. |
| 6,576,024 B1 | 6/2003 | Lang et al. |
| 6,592,630 B2 | 7/2003 | Matsunaga et al. |
| 6,616,709 B2 | 9/2003 | Ohashi et al. |
| 6,712,861 B2 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0034914 A1 | 11/2001 | Saunier et al. |
| 2001/0054206 A1 | 12/2001 | Matsunaga et al. |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0034489 A1 | 3/2002 | Wiegland et al. |
| 2002/0046431 A1 | 4/2002 | Laurent et al. |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A9 | 1/2003 | Rondeau |
| 2003/0055268 A1 | 3/2003 | Braun et al. |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2004/0258641 A1 | 12/2004 | Plos et al. |
| 2005/0005368 A1 | 1/2005 | Plos et al. |
| 2005/0005369 A1 | 1/2005 | Plos et al. |
| 2005/0008593 A1 | 1/2005 | Plos et al. |
| 2005/0028301 A1 | 2/2005 | Pastore |
| 2005/0144741 A1 | 7/2005 | Lang et al. |

FOREIGN PATENT DOCUMENTS

| | | |
|---|---|---|
| CA | 1255603 | 6/1989 |
| CH | 487 231 | 3/1970 |
| DE | 33 133 32 | 10/1984 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 3/2003 |
| DE | 101 48 844 A1 | 4/2003 |
| EP | 0 087 060 | 8/1983 |
| EP | 0 095 238 A2 | 11/1983 |
| EP | 0 080 976 B1 | 9/1986 |
| EP | 0 173 109 | 10/1989 |
| EP | 0 412 704 B1 | 4/1990 |
| EP | 0 395 282 | 10/1990 |
| EP | 0 122 324 B2 | 2/1993 |
| EP | 0 370 470 B1 | 11/1993 |
| EP | 0 337 354 B1 | 2/1994 |
| EP | 0 412 707 B1 | 2/1994 |
| EP | 0 445 342 B1 | 9/1994 |
| EP | 0 486 135 B1 | 4/1995 |
| EP | 0 503 853 B1 | 5/1996 |
| EP | 0 714 954 A2 | 6/1996 |
| EP | 0 733 355 A2 | 9/1996 |
| EP | 0 815 828 B1 | 6/1999 |
| EP | 0 970 684 A1 | 1/2000 |
| EP | 1 099 437 A1 | 5/2001 |
| EP | 1 132 076 A1 | 9/2001 |
| EP | 1 133 977 A2 | 9/2001 |

| | | |
|---|---|---|
| EP | 1 023 891 B1 | 10/2001 |
| EP | 1142559 A2 | 10/2001 |
| EP | 1 191 041 A2 | 3/2002 |
| EP | 0 582 152 B1 | 4/2003 |
| FR | 1492597 | 9/1966 |
| FR | 1583363 | 10/1969 |
| FR | 2077143 | 10/1971 |
| FR | 2080759 | 11/1971 |
| FR | 2 103 210 | 4/1972 |
| FR | 2162025 | 7/1973 |
| FR | 2190406 | 3/1974 |
| FR | 2252840 | 8/1975 |
| FR | 2270846 | 1/1976 |
| FR | 2280361 | 4/1976 |
| FR | 2316271 | 3/1977 |
| FR | 2336434 | 8/1977 |
| FR | 2368508 | 6/1978 |
| FR | 2 411 219 | 7/1978 |
| FR | 2383660 | 11/1978 |
| FR | 2393573 | 2/1979 |
| FR | 2416723 | 10/1979 |
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2589476 | 5/1987 |
| FR | 2598611 | 11/1987 |
| FR | 2692572 | 12/1995 |
| FR | 2320330 | 4/1997 |
| FR | 2741261 A | 5/1997 |
| FR | 2 773 470 | 7/1999 |
| FR | 2 773 864 | 7/1999 |
| FR | 2 797 877 | 3/2001 |
| FR | 2800612 A1 | 5/2001 |
| FR | 2811993 A1 | 1/2002 |
| FR | 2820032 | 8/2002 |
| FR | 2830189 | 4/2003 |
| GB | 759385 | 1/1953 |
| GB | 746864 | 3/1956 |
| GB | 1214394 | 12/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-236929 | 9/1998 |
| JP | 11-021214 | 1/1999 |
| JP | 11-60453 | 3/1999 |
| JP | 11-343218 | 12/1999 |
| JP | 2000-1417 | 1/2000 |
| JP | 2000-86472 | 3/2000 |
| JP | 2000-505841 | 5/2000 |
| JP | 2002-012530 | 1/2001 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-012523 | 1/2002 |
| JP | 2001-047151 | 2/2002 |
| JP | 2002-226338 | 8/2002 |
| JP | 2002-249419 | 9/2002 |
| JP | 2002-326911 | 11/2002 |
| JP | 2003-055177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 A2 | 11/1993 |
| WO | WO 94/02022 A1 | 2/1994 |
| WO | WO 95/00578 A1 | 1/1995 |
| WO | WO 95/01772 A1 | 1/1995 |
| WO | WO 95/15144 A1 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 89/36045 | 7/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 A1 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 A1 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.
Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/814,428, filed Apr. 1, 2004.
Co-pending U.S. Appl. No. 10/490,896, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Apr. 1, 2004.
English Language Derwent Abstract of DE 33 133 32 A1.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of DE 0 080 976.
English Language Derwent Abstract of DE 0 087 060.
English Language Derwent Abstract of EP 1 099 437.
English Language Derwent Abstract of FR 2,589,476.

English Language Derwent Abstract of FR 2,733,864.
English Language Derwent Abstract of FR 2,797,877.
English Language Derwent Abstract of FR 2,800,612.
English Language Derwent Abstract of JP 54-86521.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of JP 8-259426.
English Language Derwent Abstract of JP 10-236929.
English Language Derwent Abstract of JP 11-021214.
English Language Derwent Abstract of JP 11-60453.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Derwent Abstract of JP 2001-516701.
English Language Derwent Abstract of JP 2001-516706.
English Language Derwent Abstract of JP 2001-516707.
English Language Derwent Abstract of JP 2001-294519.
English Language Derwent Abstract of JP 2002-226338.
English Language Derwent Abstract of JP 2002-249419 from Japio database.
English Language Derwent Abstract of JP 2004-059468 from Japio database.
French Search Report for French Patent Application No. FR 02/16669, priority document for U.S. Appl. No. 10/742,995, Aug. 6, 2003.
French Search Report for French Patent Application No. FR 03/04021, priority document for U.S. Appl. No. 10/814,337, Dec. 8, 2003.
French Search Report for French Patent Application No. FR 03/04022, priority document for U.S. Appl. No. 10/814,336, Nov. 20, 2003.
French Search Report for French Patent Application No. FR 03/04024, priority document for U.S. Appl. No. 10/814,585, Dec. 8, 2003.
French Search Report for French Patent Application No. FR 03/04026, priority document for U.S. Appl. No. 10/814,335, Nov. 21, 2003.
French Search Report for French Patent Application No. FR 03/04027, priority document for U.S. Appl. No. 10/814,428, Nov. 28, 2003.
French Search Report for French Patent Application No. FR 03/04028, priority document for U.S. Appl. No. 10/814,236, Nov. 25, 2003.
French Search Report for French Patent Application No. FR 03/04029, priority document for U.S. Appl. No. 10/814,430, Feb. 5, 2004.
French Search Report for French Patent Application No. FR 03/04030, priority document for U.S. Appl. No. 10/814,300, Nov. 27, 2003.
French Search Report for French Patent Application No. FR 03/04031, priority document for U.S. Appl. No. 10/814,333, Jan. 8, 2004.
French Search Report for French Patent Application No. FR 03/04033, priority document for U.S. Appl. No. 10/814,334, Nov. 28, 2003.
French Search Report for French Patent Application No. FR 03/04034, priority document for co-pending U.S. Appl. No. 10/814,338, Feb. 17, 2004.
French Search Report for French Patent Application No. FR 03/04035, priority document for co-pending U.S. Appl. No. 10/814,305, Feb. 5, 2004.
International Search Report for PCT Application No. PCT/FR 02/03252, (for co-pending U.S. Appl. No. 10/490,869, Jan. 20, 2003.
Office Action mailed Nov. 3, 2005 in co-pending U.S. Appl. No. 10/490,869.
Office Action mailed Nov. 2, 2005 in co-pending U.S. Appl. No. 10/814,338.
Office Action mailed Nov. 2, 2005 in co-pending U.S. Appl. No. 10/742,995.
Office Action mailed Mar. 25, 2006 in co-pending U.S. Appl. No. 10/814,334.
Office Action mailed Mar. 15, 2006, in co-pending U.S. Appl. No. 10/814,337.
Office Action mailed Mar. 15, 2006, in co-pending U.S. Appl. No. 10/814,305.
Office Action mailed Mar. 23, 2006, in co-pending U.S. Appl. No. 10/814,300.
Jacobi, Otto and Jacobi, Gertrud, "Investigation into the reciprocal action of cosmetics and the biosphere of the stratum corneuum of the skin," Cosmetics and Toiletries, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
D. F. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci 271, 380-389 (1993).
Zviak, C., The Science of Hair Care, pp. 215 and 278 (1986).
Office Action mailed May 18, 2006 in co-pending U.S. Appl. No. 10/814,333.
Office Action mailed Mar. 24, 2006 in co-pending U.S. Appl. No. 10/814,236.
English Language Derwent Abstract of DE 33 133 32 A1 (1984).
English Language Derwent Abstract of DE 100 29 441 (2002).
English Language Derwent Abstract of DE 101 41 683 (2003).
English Language Derwent Abstract of DE 101 48 844 (2003).
English Language Derwent Abstract of DE 199 23 438 (2000).
English Language Derwent Abstract of DE 199 26 377 (2000).
English Language Derwent Abstract of DE 0 080 976 (1986).
English Language Derwent Abstract of DE 0 087 060 (1983).
English Language Derwent Abstract of EP 1 099 437 (2001).
English Language Derwent Abstract of FR 2,589,476 (1987).
English Language Derwent Abstract of FR 2,733,864 (1999).
English Language Derwent Abstract of FR 2,797,877 (2001).
English Language Derwent Abstract of FR 2,800,612 (2001).
English Language Derwent Abstract of JP 54-86521 (1979).
English Language Derwent Abstract of JP 2-200612 (1990).
English Language Derwent Abstract of JP 6-183935 (1994).
English Language Derwent Abstract of JP 6-227954 (1994).
English Language Derwent Abstract of JP 8-183716 (1996).
English Language Derwent Abstract of JP 8-208448 (1996).
English Language Derwent Abstract of JP 8-259426 (1996).
English Language Derwent Abstract of JP 10-236929 (1998).
English Language Derwent Abstract of JP 11-021214 (1999).
English Language Derwent Abstract of JP 11-60453 (1999).
English Language Derwent Abstract of JP 2000-1417 (2000).
English Language Derwent Abstract of JP 2000-086472 (2000).
English Language Derwent Abstract of JP 2001-172120 (2001).
English Language Derwent Abstract of JP 2001-261534 (2001).
English Language Derwent Abstract of JP 2001-516701 (2001).
English Language Derwent Abstract of JP 2001-516706 (2001).
Office Action mailed May 25, 2006 in co-pending U.S. Appl. No. 10/814,335.
Office Action mailed Jun. 8, 2006 in co-pending U.S. Appl. No. 10/814,430.
Office Action mailed Jul. 7, 2006 in co-pending U.S. Appl. No. 10/814,585.
Final Office Action mailed May 26, 2006 in co-pending U.S. Appl. No. 10/490,869.
Final Office Action mailed May 30, 2006 in co-pending U.S. Appl. No. 10/814,338.
Final Office Action mailed Apr. 6, 2006 in co-pending U.S. Appl. No. 10/742,995.
Mishra, J.K. et al., "Synthesis of some bischromophoric dyes containing nonabsorbing flexible bridge," Indian Journal of Chemistry, vol. 31B, pp. 118-112, Feb. 1992.

Final Office Action mailed Aug. 24, 2006 in co-pending U.S. Appl. No. 10/814,305.
Final Office Action mailed Aug. 28, 2006 in co-pending U.S. Appl. No. 10/814,300.
Final Office Action mailed Aug. 28, 2006 in co-pending U.S. Appl. No. 10/814,236.
Office Action mailed Oct. 23, 2006 in co-pending U.S. Appl. No. 10/742,995.
Office Action mailed Jan. 25, 2007 in co-pending U.S. Appl. No. 10/814,336.

* cited by examiner

PROCESS FOR DYEING HUMAN KERATIN FIBERS, HAVING A LIGHTENING EFFECT, COMPRISING AT LEAST ONE FLUORESCENT COMPOUND AND COMPOSITIONS OF THE SAME

This application claims benefit of U.S. Provisional Application No. 60/468,103, filed May 6, 2003.

The present disclosure is directed to a process for dyeing human keratin materials having a lightening effect comprising, in a cosmetically acceptable medium, at least one fluorescent dye. The present disclosure also relates to compositions comprising the at least one fluorescent dye.

It is common for individuals to wish to lighten their skin and/or hair and for this purpose to use cosmetic or dermatological compositions containing bleaching agents. The substances most commonly used as bleaching agents are hydroquinone and its derivatives, kojic acid and its derivatives, azelaic acid, arbutin and its derivatives, alone or in combination with other active agents. However, these agents are not without their drawbacks. For example, they need to be used for a long time and in large amounts in order to obtain a bleaching effect on the skin. Moreover, no immediate effect is observed on applying compositions comprising these common bleaching agents.

With regards to hydroquinone and its derivatives, for example, they are known for their cytotoxicity towards melanocytes.

Additionally, kojic acid and its derivatives can have the drawback of being expensive and consequently of not being practically useful in large amount in products for commercial mass distribution.

There is thus still a need for cosmetic compositions that allow a lighter, uniform, homogeneous skin tone of natural appearance to be obtained.

In the field of hair care, to obtain a lighter coloration, a chemical bleaching process is conventionally used. This process consists in bleaching the melanins of keratin fibers with an oxidizing system, generally comprising at least hydrogen peroxide optionally combined with persalts. This operation may optionally be performed in the presence of direct dyes and/or oxidation dyes.

This bleaching system has the drawback of degrading the fibers and of impairing their cosmetic properties. For example, with bleaching, the hair has a tendency to become coarse, more difficult to disentangle, and more fragile.

It is thus desirable to have available compositions that allow the hair and other human keratin fibers to be lightened while at the same time dyeing them, in an aesthetic manner and without degrading these fibers.

The inventors of the present disclosure propose a process for dyeing human keratin materials having a lightening effect, and also at least one fluorescent compound and compositions comprising the same, which address some of the drawbacks mentioned above.

In at least one embodiment of the present disclosure, a process for dyeing human keratin materials having a lightening effect, comprising applying to the keratin materials, a composition comprising, in a cosmetically acceptable medium, at least one fluorescent compound having the following formula:

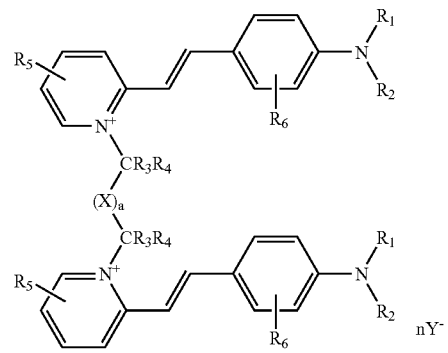

wherein:

$R_1$ and $R_2$, which may be identical or different, are chosen from:
  hydrogen atoms;
  linear and branched alkyl radicals comprising 1 to 10 carbon atoms, for example, from 1 to 4 carbon atoms, optionally interrupted with at least one entity chosen from hetero atoms and groups comprising at least one hetero atom and/or optionally substituted with at least one entity chosen from hetero atoms, groups comprising at least one hetero atom, and halogen atoms;
  aryl and arylalkyl radicals, wherein the aryl groups comprise 6 carbon atoms and the alkyl groups comprise 1 to 4 carbon atoms; the aryl group may optionally be substituted with at least one linear or branched alkyl radical comprising 1 to 4 carbon atoms optionally interrupted with at least one entity chosen from hetero atoms and groups comprising at least one hetero atom and/or optionally substituted with at least one entity chosen from hetero atoms, groups comprising at least one hetero atom, and halogen atoms;
$R_1$ and $R_2$ may optionally be linked so as to form a heterocycle with the nitrogen atom and may further comprise at least one other hetero atom, wherein the heterocycle may be optionally substituted with at least one linear or branched alkyl radical, for example, comprising 1 to 4 carbon atoms and optionally interrupted with at least one entity chosen from hetero atoms and groups comprising at least one hetero atom and/or optionally substituted with at least one entity chosen from hetero atoms, groups comprising at least one hetero atom, and halogen atoms;
$R_1$ or $R_2$ may also optionally be engaged in a heterocycle comprising the nitrogen atom to which they are attached and one of the carbon atoms of the phenyl group bearing the nitrogen atom;
$R_3$ and $R_4$, which may be identical or different, are chosen from hydrogen atoms and alkyl radicals comprising 1 to 4 carbon atoms;
$R_5$, which may be identical or different, is chosen from hydrogen atoms, halogen atoms or linear and branched alkyl radicals comprising 1 to 4 carbon atoms, optionally interrupted with at least one hetero atom;
$R_6$, which may be identical or different, is chosen from hydrogen atoms; halogen atoms; linear or branched alkyl radicals comprising 1 to 4 carbon atoms, optionally substituted with at least one entity chosen from hetero atoms, groups comprising at least one hetero atom and/or optionally interrupted with at least one entity chosen from hetero atoms, groups comprising at least one hetero atom, and halogen atoms;

X is chosen from:
linear and branched alkyl radicals comprising 1 to 14 carbon atoms and alkenyl radicals comprising 2 to 14 carbon atoms, wherein said alkyl and alkenyl radicals may be optionally interrupted with at least one entity chosen from hetero atoms and groups substituted with at least one hetero atom and/or may be optionally substituted with at least one entity chosen from hetero atoms, groups containing at least one hetero atom, and halogen atoms;

5- and 6-membered heterocyclic radicals optionally substituted with at least one entity chosen from
linear and branched alkyl radicals comprising 1 to 14 carbon atoms, optionally substituted with at least one hetero atom;
linear and branched aminoalkyl radicals comprising 1 to 4 carbon atoms, optionally substituted with at least one hetero atom; and
halogen atoms;

fused and non-fused aromatic and diaromatic radicals, optionally separated with an alkyl radical comprising 1 to 4 carbon atoms, wherein the aromatic and diaromatic radicals may optionally be substituted with at least one entity chosen from halogen atoms and from alkyl radicals comprising 1 to 10 carbon atoms optionally substituted and/or interrupted with at least one entity chosen from hetero atoms and groups bearing at least one hetero atom dicarbonyl radicals;
the group X optionally comprises at least one cationic charge;
a is equal to 0 or 1;
$Y^-$, which may be identical or different, is chosen from organic or mineral anions; and
n is an integer ranging from 2 to the number of cationic charges present in the fluorescent dye.

The present disclosure is also directed to at least one fluorescent or non-fluorescent dye, of the following formula:

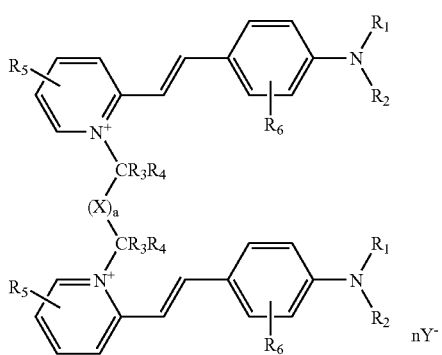

wherein:
$R_1$ and $R_2$, which may be identical or different, are chosen from:
hydrogen atoms;
linear and branched alkyl radicals comprising 1 to 10 carbon atoms, for example, from 1 to 4 carbon atoms, optionally interrupted with at least one entity chosen from hetero atoms and groups comprising at least one hetero atom and optionally substituted with at least one entity chosen from hetero atoms, groups comprising at least one hetero atom and halogen atoms;

aryl and arylalkyl radicals, wherein the aryl groups comprise 6 carbon atoms and the alkyl groups comprise 1 to 4 carbon atoms; the aryl groups may optionally be substituted with at least one entity chosen from linear and branched alkyl radicals comprising 1 to 4 carbon atoms optionally interrupted with at least one entity chosen from hetero atoms and groups comprising at least one hetero atom and optionally substituted with at least entity chosen from hetero atoms, groups comprising at least one hetero atom, and halogen atoms;

$R_1$ and $R_2$ may optionally be linked so as to form a heterocycle with the nitrogen atom to which they are attached and may further comprise at least one other hetero atom, wherein the heterocycle is optionally substituted with at least one linear or branched alkyl radical, for example, comprising 1 to 4 carbon atoms, said alkyl radical being optionally interrupted with at least one entity chosen from hetero atoms and groups comprising at least one hetero atom and being optionally substituted with at least one entity chosen from hetero atoms, groups comprising at least one hetero atom, and halogen atoms;

$R_1$ or $R_2$ may also optionally be engaged in a heterocycle comprising the nitrogen atom to which they are attached and one of the carbon atoms of the phenyl group bearing the said nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms, and linear or branched alkyl radicals comprising 1 to 4 carbon atoms, optionally interrupted with at least one hetero atom;

$R_6$, which may be identical or different, is chosen from hydrogen atoms; halogen atoms; linear and branched alkyl radicals comprising 1 to 4 carbon atoms, optionally interrupted with at least one entity chosen from hetero atoms and groups comprising at least one hetero atom and optionally substituted with at least one entity chosen from hetero atoms, and groups comprising at least one hetero atom and halogen atom;

X is chosen from:
linear and branched alkyl radicals comprising 1 to 14 carbon atoms or alkenyl radicals comprising 2 to 14 carbon atoms, said alkyl and alkenyl radicals optionally being interrupted with at least one entity chosen from hetero atoms and groups comprising at least one hetero atom and optionally being substituted with at least one entity chosen from hetero atoms, groups comprising at least one hetero atom, and halogen atoms;

5- and 6-membered heterocyclic radicals optionally substituted with at least one entity chosen from
linear or branched alkyl radicals comprising 1 to 14 carbon atoms, optionally substituted with at least one hetero atom;
linear or branched aminoalkyl radicals comprising 1 to 4 carbon atoms, optionally substituted with at least one hetero atom; and
halogen atoms;

fused and non-fused aromatic or diaromatic radicals, optionally separated with at least one alkyl radical comprising 1 to 4 carbon atoms, the aromatic and diaromatic radicals may optionally be substituted with at least one entity chosen from halogen atoms and alkyl radicals comprising 1 to 10 carbon atoms optionally substituted and/or interrupted with at least one entity chosen from hetero atoms and groups comprising at least one hetero atom dicarbonyl radicals;

the group X optionally comprising at least one cationic charge;

a is equal to 0 or 1;

$Y^-$, which may be identical or different, is chosen from organic and mineral anions;

n is an integer ranging from 2 to the number of cationic charges present in the fluorescent compound;

with the exception of the compounds for which:

X is chosen from unsubstituted linear alkyl radicals comprising 1 or 4 carbon atoms wherein a is equal to 1 or a is equal to 0; and $R_1$ and $R_2$ simultaneously comprise methyl radicals; $R_5$ and $R_6$ comprise hydrogen atoms; $R_3$ and $R_4$, which are identical, comprise hydrogen atoms;

X is chosen from ethyl, linear and branched unsubstituted $C_3$ alkyl radicals; a is equal to 1; $R_3$ and $R_4$, which are identical, are hydrogen atoms; $R_5$ is a hydrogen atom; $R_1$ and $R_2$:

are identical, and are chosen from methyl radicals, and $R_6$ is chosen from hydrogen atoms and methyl radicals in an ortho position relative to the carbon atom of the benzene ring bearing the carbon-carbon unsaturated bond;

and are identical, comprise ethyl radicals, and $R_6$ is chosen from hydrogen atoms and methoxy radicals in an ortho position relative to the carbon atom of the benzene ring bearing the carbon-carbon unsaturated bond; or are different, and are chosen from ethyl radicals and ethyl radicals substituted with an entity chosen from dimethylamino, trimethylammonium and benzyldimethylammonium groups;

X is chosen from phenyl radicals linked to the groups $CR_3R_4$ via bonds in the 1,4 position relative to each other; $R_3$ and $R_4$, which are identical, comprise hydrogen atoms; a is equal to 1; $R_5$ comprises a hydrogen atom; $R_1$ and $R_2$:

are identical, and are methyl radicals, and $R_6$ is chosen from hydrogen atoms and methyl radicals in an ortho position relative to the carbon atom of the benzene ring bearing the carbon-carbon unsaturated bond;

are identical, comprise ethyl radicals, and $R_6$ is chosen from hydrogen atoms or methoxy radicals in an ortho position relative to the carbon atom of the benzene ring bearing the carbon-carbon unsaturated bond; or are different, and are chosen from ethyl radicals and ethyl radicals substituted with an entity chosen from dimethylamino, trimethylammonium and benzyldimethylammonium groups.

Further, another embodiment of the disclosure is directed to a multi-compartment kit, comprising at least one compartment containing a composition comprising at least one fluorescent dye or non-fluorescent dye as disclosed herein and optionally at least one entity chosen from direct dyes, oxidation bases, and/ couplers, in a cosmetically acceptable medium, and at least one other compartment containing a composition comprising at least one oxidizing agent.

The present disclosure allows for dyeing, while at the same time lightening, human keratin materials without impairing them. In contrast, many of the standard processes in which it is desired to dye keratin materials while at the same time lightening them use compounds that can in the long run cause damage to the keratin materials (kojic acid, hydroquinone and oxidizing agent).

For example, the process according to the present disclosure makes it possible to obtain a coloration or a shade for which the reflectance of the materials treated in accordance with the invention, measured ranging from about 550 to about 700 nm, is greater than the reflectance of the untreated materials.

The present disclosure provides a lighter coloration than the natural coloration, with a satisfactory aesthetic effect.

Finally, in the case of compositions applied to keratin fibers, such as, for example, the hair, the disclosed compounds may possess good dyeing affinity for these fibers, and good fastness properties with respect to external agents.

However, other characteristics and advantages of the present disclosure will emerge more clearly on reading the description, the examples and the attached figure representing the reflectance as a function of the wavelength for hair treated with the composition according to the disclosure and for untreated hair.

Unless otherwise indicated, the limits of the ranges of values that are given in the description are included in these ranges.

First, the keratin materials treated in accordance with the disclosed process according to the disclosure are of human origin. In the text herein below, mention will be made to keratin materials, it being understood that they are human keratin materials. In addition, they may or may not be in the form of fibers. Thus, the keratin materials may be, for example, the skin, the hair, the eyelashes, the eyebrows, the beard or the moustache.

According to at least one aspect of the disclosure, the treated keratin material is the skin. For example, the skin has a lightness L* in the C.I.E. L*a*b* system, measured using a Minolta CM2002 colorimeter, of less than or equal to 55. It is recalled that a value of 0 for L* is equivalent to black and 100 is equivalent to white.

Non-limiting examples of the skin types corresponding to this lightness are asiatic skin, african skin, afro-american skin, hispano-american skin, indian skin and north-african skin.

According to a further embodiment of the disclosure, the treated keratin materials are in the form of fibers, and for example, of artificially pigmented fibers or artificially colored fibers. These fibers are, for example, the hair.

The artificially pigmented or colored hair has a tone height of less than or equal to 6 (dark blond) and, for example, less than or equal to 4 (chestnut).

The notion of "tone" is based on the classification of the natural shades, one tone separating each shade from the one immediately following or preceding it. This definition and the classification of the natural shades are well known to hairstyling professionals and are published in the book "Sciences des traitements capillaires [Hair treatment sciences]" by Charles Zviak, 1988, published by Masson, pp. 215 and 278.

As has been mentioned previously, the process according to the disclosure comprises applying a composition comprising at least one fluorescent dye.

For the purpose of clarity of the description, the composition and its various ingredients will first be described.

The at least one fluorescent dye present in the composition corresponds to the following general formula:

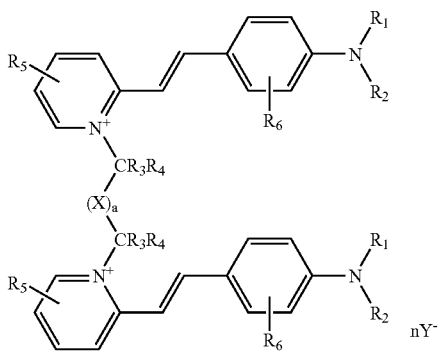

In this formula, $R_1$ and $R_2$, which may be identical or different, are chosen from:
hydrogen atoms;
linear and branched alkyl radicals comprising 1 to 10 carbon atoms and for example, from 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
aryl and arylalkyl radicals, wherein the aryl groups comprise 6 carbon atoms and the alkyl groups comprise 1 to 4 carbon atoms; the aryl groups may optionally be substituted with at least one linear or branched alkyl radical comprising 1 to 4 carbon atoms optionally interrupted with at least one entity chosen from hetero atoms and groups comprising at least one hereto atom and optionally substituted with at least one entity chosen from hetero atoms, groups comprising at least one hetero atom, and halogen atoms;
$R_1$ and $R_2$ may also be optionally linked to form a heterocycle with the nitrogen atom and may comprise at least one hetero atom, the heterocycle optionally being substituted with at least one radical chosen from linear or branched alkyl radicals, for example, comprising 1 to 4 carbon atoms, and optionally being interrupted with at least one entity chosen from hetero atoms and groups comprising at least one hetero atom and optionally substituted with at least one entity chosen from hetero atoms, groups comprising at least one hetero atom, and halogen atoms;
$R_1$ or $R_2$ may also optionally be included in a heterocycle comprising the nitrogen atom and one of the carbon atoms of the phenyl group comprising the said nitrogen atom.

As used herein, the term "hetero atom" means oxygen and nitrogen atoms.

Among the groups comprising such atoms that may be used, non-limiting mention may be made of, among others, hydroxyl, alkoxy, carbonyl, amino, ammonium, amido, i.e., —N—CO— and carboxyl, i.e., —O—CO— or —CO—O— groups.

With regard to the alkenyl groups, these groups comprise at least one unsaturated carbon-carbon bonds (e.g., —C=C—) and for example, only one carbon-carbon double bond.

In this general formula, $R_1$ and $R_2$, which may be identical or different, for example, are chosen from:
hydrogen atoms;
alkyl radicals comprising 1 to 10 carbon atoms, for example, 1 to 6 carbon atoms, further for example, 1 to 4 carbon atoms, optionally interrupted with an oxygen atom or optionally substituted with at least one entity chosen from hydroxyl, amino or ammonium radicals and chlorine and fluorine atoms;
benzyl and phenyl radicals optionally substituted with a radical chosen from alkyl and alkoxy radicals comprising 1 to 4 carbon atoms, for example, 1 or 2 carbon atoms;
nitrogen atoms, heterocyclic radicals chosen from pyrrolo, pyrrolidino, imidazolino, imidazolo, imidazolium, pyrazolino, piperazino, morpholino, morpholo, pyrazolo and triazoloradicals, optionally substituted with at least one linear or branched alkyl radical comprising 1 to 4 carbon atoms and optionally interrupted and/or optionally substituted with an entity chosen from nitrogen and oxygen atoms, and groups comprising nitrogen and oxygen atoms.

With regard to the abovementioned amino or ammonium radicals, the radicals borne by the nitrogen atom may be identical or different and may, for example, be chosen from hydrogen atoms, $C_1$-$C_{10}$ alkyl radicals, for example, $C_1$-$C_4$ alkyl radicals and arylalkyl radicals wherein, for example, the aryl radical contains 6 carbon atoms and the alkyl radical contains from 1 to 10 carbon atoms, and for example, 1 to 4 carbon atoms.

According to still another aspect of the present disclosure, the radicals $R_1$ and $R_2$, which may be identical or different are chosen from hydrogen atoms; linear and branched $C_1$-$C_6$ alkyl radicals; $C_2$-$C_6$ alkyl radicals substituted with a hydroxyl radical; $C_2$-$C_6$ alkyl radicals comprising an amino or ammonium group; $C_2$-$C_6$ chloroalkyl radicals; $C_2$-$C_6$ alkyl radicals interrupted with an entity chosen from oxygen atoms and groups comprising oxygen atoms (for example esters); aromatic radicals, such as, phenyl, benzyl or 4-methylphenyl; and heterocyclic radicals, such as, pyrrolo, pyrrolidino, imidazolo, imidazolino, imidazolium, piperazino, morpholo, morpholino, pyrazolo and triazolo radicals, optionally substituted with at least one $C_1$-$C_6$ alkyl or aromatic radical.

For example, $R_1$ and $R_2$, which may be identical or different, are chosen from hydrogen atoms, linear and branched $C_1$-$C_6$ alkyl radicals, such as methyl, ethyl, n-butyl or n-propyl radicals; 2-hydroxyethyl; alkyltrimethylammonium or alkyltriethylammonium radicals, the alkyl radical being a linear $C_2$-$C_6$ alkyl radical; (di)alkylmethylamino and (di)alkylethylamino radicals, the alkyl radical being a linear $C_1$-$C_6$ alkyl radical; —$CH_2CH_2Cl$; —$(CH_2)_n$—$OCH_3$ and —$(CH_2)_n$—$OCH_2CH_3$ wherein n is an integer ranging from 2 to 6; —$CH_2CH_2$—$OCOCH_3$; and —$CH_2CH_2COOCH_3$.

Further, $R_1$ and $R_2$, which may or may not be identical, are identical, and are chosen from methyl radicals and ethyl radicals.

$R_1$ and $R_2$, which may be identical or different, may also be chosen from heterocyclic radicals of the pyrrolidino, 3-aminopyrrolidino, 3-(dimethyl)aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo and 1H-1,2,4-triazolo radicals.

$R_1$ and $R_2$, which may be identical or different, may also be chosen from and may be linked to form a heterocycle of formula (I) and (II) below:

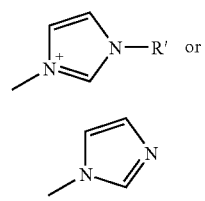 (I)

or (II)

wherein R' is chosen from hydrogen atoms, $C_1$-$C_3$ alkyl radicals, —$CH_2CH_2OH$, and —$CH_2CH_2OCH_3$.

In accordance with yet another aspect of the disclosure, $R_5$, which may be identical or different, is chosen from hydrogen atoms, fluorine and chlorine atoms, and linear and branched alkyl radicals, comprising 1 to 4 carbon atoms optionally interrupted with an entity chosen form oxygen and nitrogen atoms.

$R_5$, if it is other than hydrogen, may be, for example, in position(s) 3 and/or 5 relative to the carbon of the ring bearing the nitrogen substituted with the radicals $R_1$ and $R_2$, and for example, may be in position 3 relative to that carbon.

For further example, $R_5$, which may be identical or different, comprises hydrogen atoms; linear and branched $C_1$-$C_4$ alkyl radicals; —O—$R_{51}$ wherein $R_{51}$ comprises linear $C_1$-$C_4$ alkyl radicals; —$R_{52}$—O—$CH_3$ wherein $R_{52}$ comprises linear $C_2$-$C_3$ alkyl radicals; —$R_{53}$—$N(R_{54})_2$ wherein $R_{53}$ comprises linear $C_2$-$C_3$ alkyl radicals and $R_{54}$, which may be identical or different, is chosen from hydrogen atoms and methyl radicals.

For example, $R_5$, which may be identical or different, is chosen from hydrogen, methyl and methoxy, and $R_5$, in further example, is a hydrogen atom.

According to another aspect, $R_6$, which may be identical or different, is chosen from hydrogen atoms; linear and branched $C_1$-$C_4$ alkyl radicals; —X wherein X comprises chlorine, bromine and fluorine atoms; —$R_{61}$—O—$R_{62}$ wherein $R_{61}$ comprises linear $C_2$-$C_3$ alkyl radicals and $R_{62}$ comprises methyl radicals; —$R_{63}$—$N(R_{64})_2$ wherein $R_{63}$ comprises linear $C_2$-$C_3$ alkyl radicals and $R_{64}$, which may be identical or different, is chosen from hydrogen atoms and methyl radicals; —$N(R_{65})_2$ wherein $R_{65}$, which may be identical or different, is chosen from hydrogen atoms and linear $C_2$-$C_3$ alkyl radicals; —$NHCOR_{66}$ wherein $R_{66}$ is chosen from $C_1$-$C_2$ alkyl radicals, $C_1$-$C_2$ chloroalkyl radicals, radicals —$R_{67}$—$NH_2$, —$R_{67}$—$NH(CH_3)$, —$R_{67}N(CH_3)_2$, —$R_{67}$—$N^+(CH_3)_3$, and —$R_{67}$—$N^+(CH_2CH_3)_3$ wherein $R_{67}$ comprises $C_1$-$C_2$ alkyl radicals.

$R_6$, if it is other than hydrogen, is, for example, in position 2 and/or 4 relative to the nitrogen atom of the pyridinium ring, and further for example, in position 4 relative to that nitrogen atom.

As such, $R_6$, which may be identical or different, is chosen from hydrogen atoms and methyl or ethyl radicals, and $R_6$, for example, comprises a hydrogen atom.

With regard to $R_3$ and $R_4$, these radicals, which may be identical or different, are chosen, for example, from hydrogen atoms and alkyl radicals comprising 1 to 4 carbon atoms, and for example, methyl radicals. In further examples, $R_3$ and $R_4$ are each hydrogen atoms.

As mentioned above, X is chosen from:
linear or branched alkyl radicals comprising 1 to 14 carbon atoms and alkenyl radicals comprising 2 to 14 carbon atoms, said alkyl and alkenyl radicals being optionally interrupted with at least one entity chosen from hetero atoms and groups comprising at least one hetero atom and being optionally substituted with at least one entity chosen from hetero atoms, groups comprising at least one hetero atom, and halogen atoms;

5- and 6-membered heterocyclic radicals, optionally substituted with at least one entity chosen from
linear and branched alkyl radicals comprising 1 to 14 carbon atoms;
linear and branched aminoalkyl radicals comprising 1 to 4 carbon atoms, optionally substituted with at least one hetero atom; and
halogen atoms;

fused and non-fused aromatic and diaromatic radicals, optionally interrupted with an alkyl radical comprising 1 to 4 carbon atoms, wherein the aromatic and diaromatic radicals may optionally be substituted with at least one entity chosen from halogen atoms and alkyl radicals comprising 1 to 10 carbon atoms, wherein the alkyl radical may optionally be interrupted with at least one hetero atom and substituted with at least one entity chosen from hetero atoms and groups bearing at least one hetero atom;

dicarbonyl radicals.

In addition, the group X optionally comprises at least one cationic charge.

Thus, X may be chosen from linear and branched alkyl radicals comprising 1 to 14 carbon atoms, and alkenyl radicals comprising 2 to 14 carbon atoms, and wherein X may be optionally interrupted with at least one hetero atom chosen from oxygen and nitrogen atoms, and may be optionally substituted with at least one entity chosen from hetero atoms chosen from oxygen and nitrogen atoms, groups comprising at least one hetero atom, and halogens chosen from fluorine and chlorine atoms.

Among the groups of this type, non-limiting mention may be made, for example, of hydroxyl, alkoxy (for instance, with a radical R of the $C_1$-$C_4$ alkyl type), amino, ammonium, amido, carbonyl and carboxyl groups, i.e., —COO— or —O—CO—, such as, with a radical of alkyloxy type.

The nitrogen atom, if present, may be in a quaternized or non-quaternized form. When a nitrogen atom is present, the at least one other radical borne by the quaternized or non-quaternized nitrogen atom may be identical or different, and may be chosen from hydrogen atoms and $C_1$-$C_4$ alkyl radicals, such as, methyl.

According to yet another aspect of the present disclosure, the group X may comprise at least one chosen from 5- and 6-membered heterocyclic radicals chosen from imidazolo, pyrazolo, triazino and pyridino radicals, which may be optionally substituted with at least one entity chosen from linear and branched alkyl radicals comprising 1 to 14 carbon atoms, for instance, from 1 to 10 carbon atoms, and such as, from 1 to 4 carbon atoms; and linear and branched aminoalkyl radicals comprising 1 to 10 carbon atoms, for example, from 1 to 4 carbon atoms, optionally substituted with an entity chosen from groups comprising at least one hetero atom, such as, hydroxyl radicals, and halogen atoms. The amino group may be linked to the heterocycle.

In accordance with another aspect of the present disclosure, X may be chosen from aromatic radicals, for example, containing 6 carbon atoms, or fused or non-fused diaromatic radicals, for example, comprising 10 to 12 carbon atoms, optionally separated with an alkyl radical comprising 1 to 4 carbon atoms, wherein the diaromatic radicals may optionally be substituted with at least one entity chosen from halogen atoms and alkyl radicals comprising 1 to 10 carbon atoms, such as from 1 to 4 carbon atoms, wherein the alkyl radicals may optionally be interrupted with at least one entity chosen from oxygen and nitrogen atoms, and groups comprising at least one hetero atom, for instance, carbonyl, carboxyl, amido, amino, and ammonium radicals.

The aromatic radical, for example, a phenyl radical, may be linked to the groups $CR_3R_4$ via bonds in positions 1,2; 1,3 and 1,4, for example, in positions 1,3 and 1,4. If the phenyl radical linked via bonds in positions 1,4 bears one or two substituents, the at least one substituent may be located in position 1,4 relative to one of the groups $CR_3R_4$. If the phenyl radical linked via bonds in positions 1,3 bears one or two substituents, this or these substituent(s) are preferably located in position 1 and/or 3 relative to one of the groups $CR_3R_4$.

In the case where X is diaromatic, it, may be, for example, non-fused and comprises two phenyl radicals optionally separated with an entity chosen from single bonds, i.e., a carbon of each of the two rings and alkyl radicals, for example, $CH_2$ and $C(CH_3)_2$ type. According to one embodiment, the aromatic radicals do not have to bear a substituent. It should be noted that the diaromatic radical may be linked to the groups $CR_3R_4$ via bonds in positions 4,4'.

As examples of the groups from which X may be chosen, non-limiting mention may be made of, for example, linear and branched alkyl radicals comprising 1 to 13 carbon atoms, such as methylene, ethylene, propylene, isopropylene, n-butylene, pentylene and hexylene; 2-hydroxypropylene and 2-hydroxy-n-butylene; $C_1$-$C_{13}$ alkylene radicals interrupted with at least one hetero atom chosen from nitrogen and oxygen atoms, and optionally substituted with at least one entity chosen from nitrogen atoms, oxygen atoms, and groups bearing at least one hetero atom, for instance, hydroxyl, amino, ammonium, carbonyl and carboxyl groups, for example, —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+(CH_3)_2$—$CH_2CH_2$—, CO—CO—, 3,3-di-methylpentylene, 2-acetoxyethylene, butylene-1,2,3,4-tetraol; —CH=CH—; aromatic and diaromatic radicals substituted with at least one entity chosen from halogen atoms, and alkyl radicals, with at least one group comprising at least one hetero atom, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate and 1,4-bis(amidomethyl)phenyl; heterocyclic radicals, for example, pyridine, and derivatives thereof, including 2,6-bispyridine, imidazole, imidazolium and triazine.

According to still another aspect of the present disclosure, X may be chosen from linear and branched $C_1$-$C_{13}$ alkyl radicals; —$CH_2CH(OH)CH_2$—; —$CH_2CH(Cl)CH_2$—; —$CH_2CH_2$—$OCOCH_2$—; —$CH_2CH_2COOCH_2$—; —Ra—O—Rb— wherein Ra is chosen from linear $C_2$-$C_6$ alkyl radicals and Rb is chosen from linear $C_1$-$C_2$ alkyl radicals; —Rc—N(Rd)—Re— wherein Rc is chosen from $C_2$-$C_9$ alkyl radicals, Rd is chosen from hydrogen atoms and $C_1$-$C_2$ alkyl radicals and Re is chosen from $C_1$-$C_6$ alkyl radicals; —Rf—$N^+(Rg)_2$—Rh— wherein Rf is chosen from linear $C_2$-$C_9$ alkyl radicals, Rg, which are, for example, identical, are chosen from $C_1$-$C_2$ alkyl radicals and Rh is chosen from linear $C_1$-$C_6$ alkyl radicals; and —CO—CO—.

X may comprise an imidazole radical, optionally substituted with at least one alkyl radical comprising 1 to 14 carbon atoms, such as, from 1 to 10 carbon atoms, still further, from 1 to 4, and for example, the divalent radicals of formula (III);

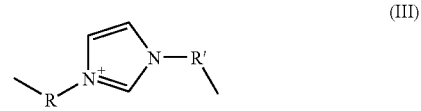

wherein Ri and Rj, which may be identical or different, are chosen from linear $C_1$-$C_6$ alkyl radicals;

X may also be chosen from the divalent triazine-based radicals of the following formula below:

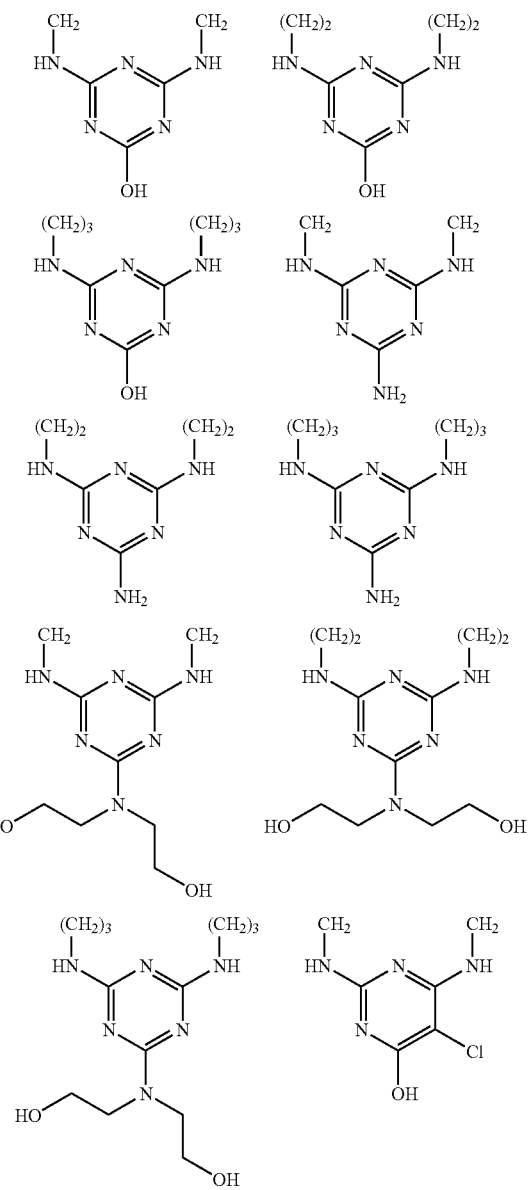

According to another aspect of the present disclosure, X may be chosen from the divalent aromatic radicals below:

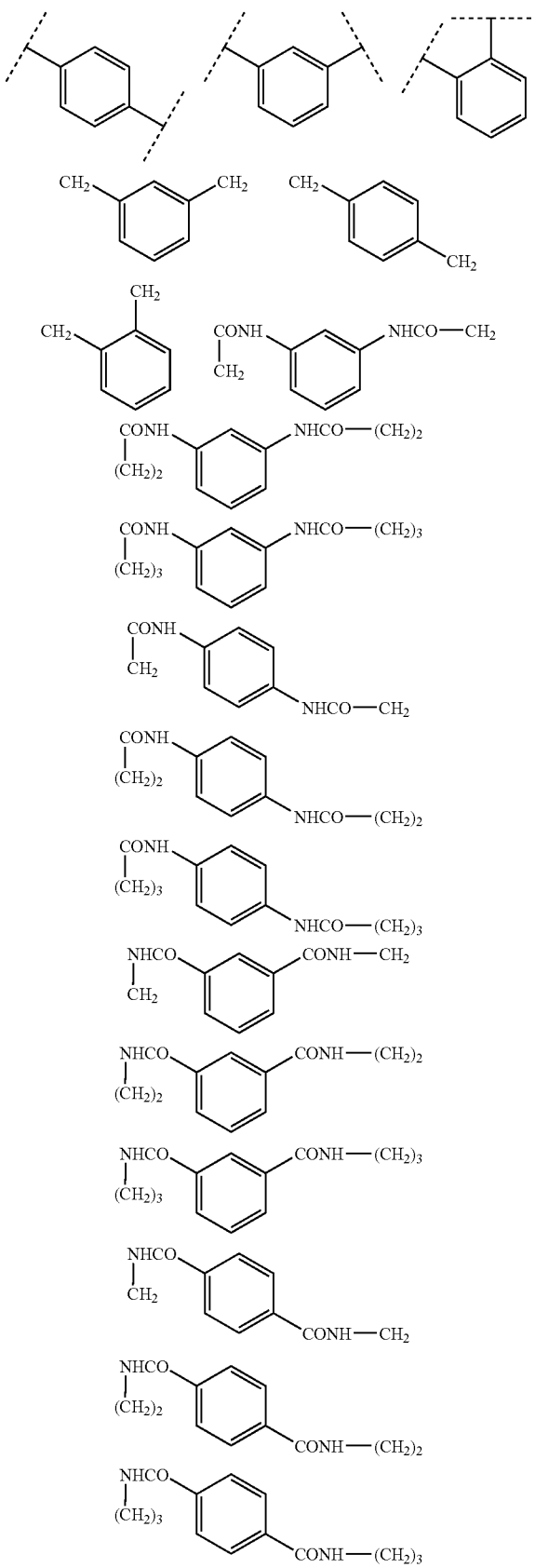

In the general formula of the fluorescent compounds described herein, Y⁻ represents an organic or mineral anion. If there are several anions Y⁻, these anions may be identical or different.

Among the anions of mineral origin that may be mentioned, without limited, are anions derived from halogen atoms, such as chlorides, iodides, sulphates, bisulphates, nitrates, phosphates, hydrogen phosphates, dihydrogen phosphates, carbonates and bicarbonates.

Among the anions of organic origin that may be used, non-limiting mention may be made of anions derived from the salts of saturated or unsaturated, aromatic or non-aromatic monocarboxylic or polycarboxylic, sulphonic or sulphuric acids, optionally substituted with at least one entity chosen from halogen atoms, and hydroxyl and amino radicals. Non-limiting examples of organic anions include acetates, hydroxyacetates, aminoacetates, (tri)chloroacetates, benzoxyacetates, propionates and derivatives bearing a chlorine atom, fumarates, oxalates, acrylates, malonates, succinates, lactates, tartrates, glycolates, citrates, benzoates and derivatives comprising a methyl or amino radical, alkyl sulphates, tosylates, benzenesulphonates, and toluenesulphonates.

For example, the at least one anion Y, which may be identical or different, may be chosen from chloride, sulphate, methosulphate, and ethosulphate.

As discussed above, the integer n ranges from 2 and to the number of cationic charges present in the fluorescent dye.

For example, the fluorescent dyes according to the present disclosure may be symmetrical compounds.

These fluorescent compounds may be synthesized by reacting, in a first step, x-picoline with a reagent comprising two leaving groups that may be chosen from halogen atoms, such as bromine, chlorine, tolylsulphonyl radicals and methanesulphonyl radicals.

This first step may optionally take place in the presence of a solvent, for instance dimethylformamide.

The number of moles of α-picoline is generally 2 per mole of reagent comprising the leaving groups.

In addition, the reaction is usually performed at the reflux temperature of the reagent and/or of the solvent, if a solvent is present.

The product derived from this first step may then be placed in contact with a corresponding aldehyde having the following formula:

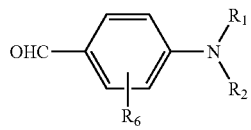

wherein $R_1$, $R_2$ and $R_6$ have the same meanings as disclosed herein above.

The reaction may be performed in the presence of a suitable solvent, which may be, for example, at reflux.

It is also possible to use an aldehyde for which $R_1$, $R_2$, and $R_6$ comprise hydrogen atoms. Then one may perform, in accordance with standard methods, the substitution of these hydrogen atoms with suitable radicals as described in the general formula once the second step is complete.

Reference may be made especially to syntheses as described in U.S. Pat. No. 4,256,458.

It should be noted that, in U.S. Pat. No. 4,256,458, the compounds are not described as being applicable to the dyeing of human keratin materials, and even less so to dyeing with a lightening effect without the need to use a specific oxidizing compound. All the compounds described in U.S. Pat. No. 4,256,458 are applied for dyeing in the paper industry.

The fluorescent dyes described herein are dyes that absorb light in the visible part of the spectrum and possibly in the ultraviolet region, and may re-emit a fluorescent light in the visible portion of the spectrum, with a longer wavelength than that of the absorbed light. The wavelength of the re-emitted light ranges from 500 to 650 nm.

In accordance with the present disclosure, the at least one fluorescent dye may be in a form that is soluble or insoluble in the medium of the composition, at room temperature ranging from 15° to 25° C.

For example, the at least one fluorescent dye is chosen from dyes that are soluble in the medium of the composition.

According to another aspect of the process of the disclosure, the solubility of the fluorescent dye in the medium of the composition is at least 0.001 g/l, , for example, at least 0.5 g/l, for further example, at least 1 g/l, and further at least 5 g/l, at a temperature ranging from 15° to 25° C.

The fluorescent dyes of the present disclosure may be used with additional fluorescent compounds that are soluble in the medium.

As examples of a family of compounds that may be used, non-limiting mention may be made of the fluorescent dyes chosen from the following families: naphthalimides; cationic or non-cationic coumarins; xanthenodiquinolizines such as, sulphorhodamines; azaxanthenes; naphtholactams; azlactones; oxazines; thiazines; dioxazines, pyrenes, and nitrobenzoxadiazoles.

Further examples that may be mentioned comprise:
the compounds having the following structure:

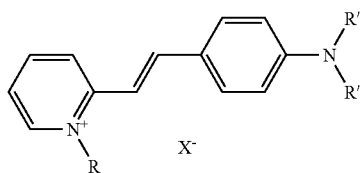

wherein formula R is chosen from methyl and ethyl radicals; R' is chosen from methyl radicals and $X^-$ is chosen from anions, such as, iodide, sulphate and methosulphate.

An example of a compound of this formula that may be used, includes the Photosensitizing Dye NK-557 sold by the company Ubichem, wherein R is ethyl radical, R' is a methyl radical and $X^-$ is an iodide.

Brilliant Yellow B6GL sold by the company Sandoz and having the following structure:

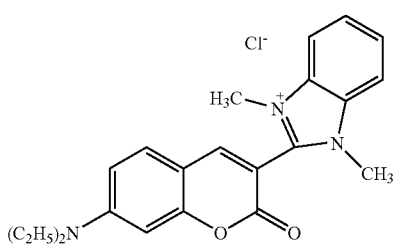

Basic Yellow 2, or Auramine O, sold by the companies Prolabo, Aldrich or Carlo Erba and having the following structure:

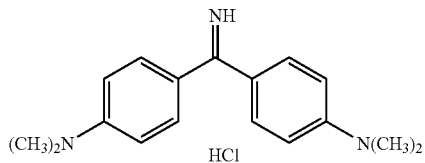

4,4'-(imidocarbonyl)bis(N,N-dimethylaniline) monohydrochloride—CAS number 2465-27-2.

Moreover, the disclosed compounds herein may also be used with additional fluorescent compounds that are insoluble in the medium, among which non-limiting mention may be made of compounds based on zinc oxide or zinc sulphide, and also organic fluorescent compounds manufactured from fluorescent dyes that are predissolved in a support resin so as to obtain a solid that is then ground.

According to yet another aspect of the present disclosure, the amount of fluorescent compound is present in an amount ranging from 0.01% to 20% by weight relative to the total weight of the composition, for example from 0.05% to 10% by weight relative to this reference, further for example, from 0.1% to 5% by weight relative to the total weight of the composition.

With regard to the amount of the at least one additional fluorescent compound, if present, from the at least one additional fluorescent compound is in an amount ranging from 0.05% to 10% by weight relative to the total weight of the composition, for example, from 0.1% to 5% by weight relative to the same reference.

The cosmetically acceptable medium generally comprises at least water or a mixture of water and of at least one organic solvent.

Examples of the at least one organic solvent that may be used include at least one solvent chosen from linear or branched alkanols, comprising 1 to 4 carbon atoms, such as, ethanol or isopropanol; polyols and polyol ethers, such as, glycerol, 2-butoxyethanol, propylene glycol, propylene glycol monomethyl ether or monoethyl ether, diethylene glycol monomethyl ether; dimethoxyethane; aromatic alcohols, such as, benzyl alcohol or phenoxyethanol, ketones comprising 3 to 4 carbon atoms, and $C_1$-$C_4$ alkyl acetates.

By way of example, the solvent, if present, is in an amount ranging from 1% to 40% by weight relative to the total weight of the composition, and for example, ranging from 5% to 30% by weight relative to the same reference.

The pH of the composition employed in the process according to the present disclosure ranges from 3 to 12, and for example, ranges from 5 to 11.

The pH may be adjusted to the desired value by means of acidifying or basifying agents normally used.

Examples of acidifying agents that may be used include mineral or organic acids, chosen from, for instance, hydrochloric acid; orthophosphoric acid; sulphuric acid; carboxylic acids; for example, acetic acid, tartaric acid, citric acid and lactic acid; and sulphonic acids.

Examples of basifying agents that may be used, non-limiting mention may be made, are aqueous ammonia, alkaline carbonates, alkanolamines such as monoethanolamine, diethanolamine and triethanolamine and derivatives thereof, sodium hydroxide, potassium hydroxide and the compounds of formula (A) below:

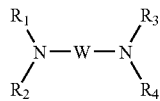 (A)

wherein W may be a propylene residue optionally substituted with an entity chosen from hydroxyl groups and $C_1$-$C_6$ alkyl radicals; $R_1$, $R_2$, $R_3$ and $R_4$, which may be identical or different, are chosen from hydrogen atoms and $C_1$-$C_6$ alkyl radicals optionally comprising at least one hydroxyl radical.

The disclosed composition may also comprise at least one direct non-fluorescent dye.

For example, the at least one direct non-fluorescent dye can be chosen from nonionic, cationic and anionic dyes.

This at least one direct dye is chosen from nitrobenzene dyes, azo dyes, azomethine dyes, methine dyes, anthraquinone dyes, naphthoquinone dyes, benzoquinone dyes, phenothiazine dyes, indigoid dyes, xanthene dyes, phenanthridine dyes, phthalocyanin dyes and triarylmethane-based dyes.

The following, non-limiting examples, of red or orange nitrobenzene dyes may be chosen from:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine and
1-amino-2-nitro-4-hydroxy-5-methylbenzene.

In addition to and/or replacing the red or orange nitrobenzene dyes, one or more additional direct dyes may be chosen from yellow, green-yellow, blue or violet nitrobenzene dyes, azo dyes, anthraquinone dyes, naphthoquinone dyes, benzoquinone dyes, indigoid dyes, and triarylmethane-based dyes.

These additional direct dyes may, for example, be basic dyes, among which non-limiting mention may be made to the dyes known in the Colour Index, 3rd edition, under the names "Basic Brown 16", "Basic Brown 17", "Basic Yellow 57", "Basic Red 76", "Basic Violet 10", "Basic Blue 26" and "Basic Blue 99", or acidic direct dyes, among which non-limiting mention may be made, for example, to the dyes known in the Colour Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", or alternatively cationic direct dyes such as those described in patent applications WO 95/01772, WO 95/15144 and EP 714 954, the entire disclosure and subject matter of which is incorporated herein by reference.

The additional yellow and green-yellow nitrobenzene direct dyes that may be used include, for example, are the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene and
4-(β-hydroxyethyl)amino-3-nitrobenzamide.

The additional blue or violet nitrobenzene direct dyes that may be used include, for example, compounds chosen from:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitroparaphenylenediamines having the following formula:

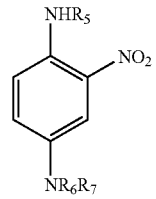

wherein:
$R_6$ is chosen from $C_1$-$C_4$ alkyl, β-hydroxyethyl, β-hydroxypropyl, and γ-hydroxypropyl radicals;
$R_5$ and $R_7$, which may be identical or different, are chosen from β-hydroxyethyl, β-hydroxypropyl, γ-hydroxypropyl and β,γ-dihydroxypropyl radicals, at least one of the radicals $R_6$, $R_7$ or $R_5$ are chosen from γ-hydroxypropyl radicals and $R_6$ and $R_7$ not simultaneously being able to denote a β-hydroxyethyl radical when $R_6$ is a γ-hydroxypropyl radical, such as those described in French patent FR 2 692 572.

When present, the at least one direct non-fluorescent dye is present in an amount ranging from 0.0005% to 12% by weight, relative to the total weight of the composition, and for example, ranging from 0.005% to 6% by weight, relative to the total weight of the composition.

In the case where the composition is employed for dyeing keratin fibers, such as the hair, with a lightening effect, the disclosed composition may still furthermore comprise at least one oxidation base.

The oxidation base may be chosen from the oxidation bases conventionally used for oxidation dyeing, such as, para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be used, non-limiting mention may be madeto para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the bis(phenyl)alkylenediamines that may be used, non-limiting mention may be made to, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

Among the para-aminophenols that may be used, non-limiting mentionmay be made to, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be used, non-limiting mentionmay be made to, 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be used, non-limiting mention may be made of pyridine derivatives, pyrimidine derivatives and pyrazole derivatives, and the addition salts thereof with an acid or with an alkaline agent.

The at least one oxidation base, if present, is in an amount ranging from 0.0005% to 12% by weight of the total weight of the composition and for example, ranges from 0.005% to 6% by weight relative to the same reference.

When it is intended for oxidation dyeing of keratin fibers such as the hair, the composition may also comprise at least one coupler that may modify and/or enrich with glints the shades obtained using the disclosed fluorescent compound and the oxidation base.

The at least one coupler may be chosen from the couplers conventionally used in this field, and among which non-limiting mention may be made to, meta-phenylenediamines, meta-aminophenols, meta-diphenols, heterocyclic couplers, and the addition salts thereof with an acid or with an alkaline agent.

These couplers are, for example, chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-di-hydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

The at least one coupler, if present, is in an amount ranging from 0.0001% to 10% by weight of the total weight of the composition and for example, from 0.005% to 5% by weight relative to the same reference.

In general, the addition salts with an acid, i.e., the oxidation bases and couplers that may be used in the compositions of the disclosure, are chosen, for example, from the hydrochlorides, hydrobromides, sulphates, citrates, succinates, tartrates, tosylates, benzenesulphonates, lactates and acetates.

The addition salts with an alkaline agent, i.e., the oxidation bases and couplers that may be used in the compositions of the disclosure are chosen, for example, from the addition salts with alkali metals and alkaline-earth metals, with ammonia and with organic amines, including alkanolamines and the compounds of formula (I).

If the composition according to the process of the invention is intended for dyeing keratin fibers, for example, the hair, the composition may include at least one oxidizing agent. The at least one oxidizing agent is chosen, for example, from hydrogen peroxide, urea peroxide, alkali metal bromates, persalts, such as, perborates and persulphates, and enzymes, such as, peroxidases and two-electron or four-electron oxidoreductases. According to tone embodiment, hydrogen peroxide or enzymes are used.

The at least one oxidizing agent, if present, is in an amount ranging from 0.001 to 10% by weight relative to the weight of the ready-to-use dye composition.

The compositions employed in the process according to the disclosure may also comprise various adjuvants conventionally used in compositions of this type, such as anionic, cationic or nonionic surfactants or mixtures thereof, anionic, cationic, nonionic, amphoteric or zwitterionic polymers or mixtures thereof, mineral or organic thickeners, antioxidants, penetrating agents, sequestering agents, fragrances, buffers, dispersants, conditioners, for instance cations, cationic or amphoteric polymers, volatile or non-volatile, modified or unmodified silicones, film-forming agents, ceramides, preserving agents, stabilizers and opacifiers.

Among the thickeners that may be used, non-limiting mention may be made to, thickening systems based on associative polymers that are well known to those skilled in the art, and for example, those of the nonionic, anionic, cationic and amphoteric nature.

The at least one surfactant, if present, is in an amount ranging from 0.01% to 40% by weight relative to the weight of the composition, for example, from 0.1% to 30% by weight, relative to the weight of the composition.

Needless to say, a person skilled in the art will take care to select any of these optional additional compound(s) such that the advantageous properties intrinsically associated with the composition are not, or are not substantially, adversely affected by the envisaged addition.

The cosmetic composition employed for dyeing keratin fibers, such as the hair, may be in various forms, such as lotions, shampoos, creams, gels, pastes, or in any other suitable form.

In a further aspect of the present disclosure, the composition is in the form of a lightening dye shampoo and further comprises, in a cosmetically acceptable aqueous medium, at least one fluorescent dye as defined above, and at least one surfactant.

For example, the fluorescent compound is in a form that is soluble in the medium.

The at least one surfactant present in the shampoo may be chosen from anionic, cationic, amphoteric and non-ionic surfactants. As such, an example of nonionic surfactants that may be mentioned is alkylpolyglucosides.

In these shampoos, the at least one surfactant is present in an amount ranging from 4% to 30% and, for example, from about 8% to 20% by weight, relative to the total weight of the shampoo composition.

According to another aspect of the present disclosure, a process comprises applying a composition to keratin fibers, for example, to the hair, with the aim of producing a temporary or transient coloration with a lightening effect on these keratin fibers, which can be removed at the first shampoo wash or by using a makeup remover. This composition, for example, comprises at least one fluorescent dye. According to this aspect, the fluorescent dye is in a form that is insoluble in the medium of the composition.

As provided above, besides the fluorescent dye, the composition may further comprise at least one non-fluorescent pigment. These non-fluorescent pigments are usually chosen from cosmetically and/or dermatologically acceptable organic or mineral pigments.

These disclosed dyes may be in the form of a powder or a pigmentary paste. Reference may be made, for example, to patent application EP 808 150 as regards the list of pigments that may be used.

The non-fluorescent pigments, if present in the composition, are added in an amount such that they do not mask the fluorescence effect provided by the disclosed fluorescent dye.

For purely indicative purposes, the non-fluorescent pigment, if present, is in an amount ranging from 0.01% to 10% by weight relative to the weight of the composition and, for example, from 0.05% to 3% by weight, relative to the same reference.

The pH of the compositions used in the context of this aspect of the disclosure ranges from 6 to 8 and for example, from 6 to 7.5.

Such compositions may further comprise at least one film-forming polymer, which may be in a form that is soluble or dispersed in the cosmetically acceptable medium of the composition.

In order to improve, as desired, the properties of the film formed, the composition may also comprise at least one plasticizer.

These compositions may further comprise various adjuvants. These adjuvants may be chosen from, for instance, insoluble or soluble, volatile or non-volatile silicones; quaternized or non-quaternized proteins; sunscreens; surfactants; antifoams; moisturizers; humectants; emollients; plant oils or synthetic oils; preserving agents or sequestering agents; antioxidants; fragrances; acidifying or basifying agents; pigment-suspending agents; and thickeners.

The compositions used in this aspect of the present disclosure may be in various forms, such as more or less thickened liquids, creams or gels.

For example, the disclosed composition may be in the form of mascara for the eyelashes or hair mascara, to be applied especially with a brush or a comb.

According to yet another aspect of the present disclosure, a process for coloring or lightening the skin comprises applying to the skin a composition comprising at least one fluorescent dye described herein.

According to this aspect, the at least the fluorescent dye may be in a form that is insoluble in the medium of the composition. The composition may comprise a fatty phase, a fraction of which is not volatile, i.e., it does not evaporate at a temperature ranging from 15° to 25° C. This fatty phase may constitute the continuous phase or the dispersed phase of the composition.

This non-volatile fraction may be chosen from non-volatile oils, waxes, gums, resins and/or pasty fatty substances of animal, plant, mineral or synthetic origin.

For example, the non-volatile fraction, if present, is in an amount ranging from 1% to 85% and for example, from 1% to 30% by weight, relative to the total weight of the composition.

The compositions according to this aspect of the disclosure may also comprise at least one "soft-focus" filler. The term "filler" should be understood as meaning colorless or white, mineral or synthetic, lamellar or non-lamellar particles intended to give body or rigidity to the composition, and/or softness, a matt effect and uniformity to the makeup result. Moreover, a "soft-focus" filler is a filler that furthermore gives transparency to the complexion and a hazy effect. This soft-focus effect is associated with the spectral reflectance of the filler.

The at least one "soft-focus" filler thus may be chosen from silica, for example, the silica microbeads SB-700 or SB-150 from Miyoshi; talc, for example, Talc P3 from Nippon Talc; silica/$TiO_2$ or silica/zinc oxide composites; polyethylene powder; starch powder; nylon powder, for example Orgasol 2002 Extra D Nat Cos from Atochem; and styrene/acrylic copolymer powders.

For example, these fillers may have a mean particle size of less than or equal to 15 µm and, for instance, less than or equal to 3 µm. For further example, these fillers are non-spherical.

As such, if the at least one filler is present, the filler is in an amount ranging from 0.1% to 20% and, for example, from 8% to 15% by weight, relative to the total weight of the composition.

The composition according to this aspect may further comprise additives that are conventional in the field. For instance, these additives may be chosen from hydrophilic or lipophilic organic UV-screening agents and mineral screening agents. If present, the additive is present in an amount ranging from 0.1% to 20% by weight, relative to the weight of the composition.

Moreover, at least one moisturizer may be present in this aspect of the disclosed composition. For example, the at least one moisturizer may be chosen from urea or its derivatives; polyols, for instance glycerol or sorbitol; and lipid vesicles emulsified, for example, using a nonionic surfactant in the composition, for instance proteins, tocopherols, amino acids, and allantoin.

The pH of composition according to this aspect of the disclosure ranges from 6.5 to 7.5. For example, the composition may be in the form of a cream, a gel or a milk. For further example, the composition may be a foundation.

As mentioned previously, the compositions used in the context of these aspects and for which the nature of the constituents and their proportions have just been described, are intended to be applied to keratin materials.

In accordance with another aspect of the present disclosure, the composition is applied without rinsing and the medium is then evaporated or left to evaporate. This method is suitable in the case where the keratin material is the skin or if the composition is intended to be applied to keratin fibers in order to temporarily dye them.

According to a further aspect of the present disclosure, a process comprises:
a) applying the disclosed composition to the keratin materials for a time that is sufficient to develop the desired coloration and lightening,
b) rinsing the keratin materials,
c) optionally washing and rinsing the keratin materials, and
d) drying the said keratin materials.

This process may be suitable when the treated keratin materials are fibers such as the hair, the moustache, the beard or the eyebrows.

The composition with which the fibers treated in step c) are optionally washed may be, for example, a shampoo.

The time required to develop the coloration and to obtain the lightening effect on the keratin fibers ranges from 5 to 60 minutes and, for example, from 5 to 40 minutes.

In addition, the temperature desired to develop the coloration and to obtain the lightening effect on the keratin fibers ranges from room temperature, i.e., ranging from 15° to 25° C., to 80° C. and, for example, from 15° to 40° C.

In the case of direct dyeing or oxidation dyeing, the process according to the disclosure comprises at least separately storing, a first composition comprising, in a medium that is suitable for dyeing, at least one fluorescent dye and optionally at least one of a direct dye, an oxidation base, and a coupler, and a second composition containing, in a medium that is suitable for dyeing, at least one oxidizing agent; and then in mixing them together at the time of use, followed by applying this mixture to the keratin fibers for a time that is sufficient to develop the desired coloration and lightening, after which the keratin fibers are rinsed; the said keratin fibers are optionally washed with a cleansing composition and are rinsed; and the keratin fibers are then dried or are left to dry.

Another aspect of the present disclosure is at least one fluorescent or non-fluorescent compound corresponding to the formula disclosed herein, wherein:

$R_1$ and $R_2$, which may be identical or different, are chosen from:

hydrogen atoms;

linear and branched alkyl radicals comprising 1 to 10 carbon atoms and for example, from 1 to 4 carbon atoms, which may optionally be interrupted with at least one entity chosen from hetero atoms and groups comprising at least one hetero atom and optionally be substituted with at least one entity chosen from hetero atoms, groups comprising at least one hetero atom, and halogen atoms;

aryl and arylalkyl radicals, wherein the aryl groups comprise 6 carbon atoms and the alkyl groups comprising 1 to 4 carbon atoms; and further wherein the aryl groups may optionally be substituted with at least one radical chosen from linear and branched alkyl radicals comprising 1 to 4 carbon atoms, which may be optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ and $R_2$ may optionally be linked so as to form a heterocycle with the nitrogen atom to which they are attached and may further comprise at least one other hetero atom, wherein the heterocycle may be optionally substituted with at least one linear or branched alkyl radical, for example, comprising 1 to 4 carbon atoms and optionally interrupted with at least one entity chosen from hetero atoms and groups comprising at least one hetero atom and/or optionally substituted with at least one entity chosen from hetero atoms, groups comprising at least one hetero atom, and halogen atoms;

$R_1$ or $R_2$ may also optionally be engaged in a heterocycle comprising the nitrogen atom to which they are attached and one of the carbon atoms of the phenyl group bearing the nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms or linear and branched alkyl radicals comprising 1 to 4 carbon atoms, optionally interrupted with at least one hetero atom;

$R_6$, which may be identical or different, is chosen from hydrogen atoms; halogen atoms; linear or branched alkyl radicals comprising 1 to 4 carbon atoms, optionally substituted with at least one entity chosen from hetero atoms, groups comprising at least one hetero atom and/or optionally interrupted with at least one entity chosen from hetero atoms, groups comprising at least one hetero atom, and halogen atoms;

X is chosen from:

linear and branched alkyl radicals comprising 1 to 14 carbon atoms and alkenyl radicals comprising 2 to 14 carbon atoms, which may be optionally interrupted with at least one entity chosen from hetero atoms and groups substituted with at least one hetero atom and/or optionally substituted with at least one entity chosen from hetero atoms, groups containing at least one hetero atom, and halogen atoms;

5- and 6-membered heterocyclic radicals optionally substituted with at least one entity chosen from
linear and branched alkyl radicals comprising 1 to 14 carbon atoms, optionally substituted with at least one hetero atom;

linear and branched aminoalkyl radicals comprising 1 to 4 carbon atoms, optionally substituted with at least one hetero atom; and halogen atoms;

fused and non-fused aromatic and diaromatic radicals, optionally separated with an alkyl radical comprising 1 to 4 carbon atoms, wherein the aromatic and diaromatic radicals may optionally be substituted with at least one entity chosen from halogen atoms and from alkyl radicals comprising 1 to 10 carbon atoms optionally substituted and/or interrupted with at least one entity chosen from hetero atoms and groups bearing at least one hetero atom dicarbonyl radicals;

the group X optionally comprises at least one cationic charge;

a is equal to 0 or 1;

$Y^-$, which may be identical or different, is chosen from organic and mineral anions; and n is an integer ranging from 2 to the number of cationic charges present in the fluorescent dye;

with the exception of the compounds for which:

X is chosen from unsubstituted linear alkyl radicals comprising 1 or 4 carbon atoms wherein a is equal to 1 or a is equal to 0; and $R_1$ and $R_2$ simultaneously comprise methyl radicals; $R_5$ and $R_6$ comprise hydrogen atoms; $R_3$ and $R_4$, which are identical, comprise hydrogen atoms;

X is chosen from ethyl, linear and branched unsubstituted $C_3$ alkyl radicals; a is equal to 1; $R_3$ and $R_4$, which are identical, are hydrogen atoms; $R_5$ is a hydrogen atom; $R_1$ and $R_2$:

are identical, and are chosen from methyl radicals, and $R_6$ is chosen from hydrogen atoms and methyl radicals in an ortho position relative to the carbon atom of the benzene ring bearing the carbon-carbon unsaturated bond;

and are identical, comprise ethyl radicals, and $R_6$ is chosen from hydrogen atoms and methoxy radicals in an ortho position relative to the carbon atom of the benzene ring bearing the carbon-carbon unsaturated bond; or are different, and are chosen from ethyl radicals and ethyl radicals substituted with an entity chosen from dimethylamino, trimethylammonium and benzyldimethylammonium groups;

X is chosen from phenyl radicals linked to the groups $CR_3R_4$ via bonds in the 1,4 position relative to each other; $R_3$ and $R_4$, which are identical, comprise hydrogen atoms; a is equal to 1; $R_5$ comprises a hydrogen atom; $R_1$ and $R_2$:

are identical, and are methyl radicals, and $R_6$ is chosen from hydrogen atoms and methyl radicals in an ortho position relative to the carbon atom of the benzene ring bearing the carbon-carbon unsaturated bond;

are identical, comprise ethyl radicals, and $R_6$ is chosen from hydrogen atoms or methoxy radicals in an ortho position relative to the carbon atom of the benzene ring bearing the carbon-carbon unsaturated bond; or are different, and are chosen from ethyl radicals and ethyl radicals substituted with an entity chosen from dimethylamino, trimethylammonium and benzyldimethylammonium groups;

According to another aspect of the present disclosure, the compounds that are excluded are those wherein:

X may be chosen from linear alkyl radicals comprising 1 carbon atom wherein a is equal to 1 or a is equal to 0; and $R_1$ and $R_2$ are chosen from methyl radicals; $R_5$ and $R_6$ are chosen from hydrogen atoms;

X is chosen from linear and branched $C_2$-$C_3$ alkyl radicals; a is equal to 1; $R_1$ and $R_2$, which are identical, are chosen from methyl radicals and ethyl radicals, or are different, and may be chosen from ethyl radicals and ethyl radicals substituted with an entity chosen from dimethylamino, trimethylammonium and benzyldimethylammonium groups; $R_5$ is chosen from a hydrogen atom; $R_6$ may be chosen from hydrogen atoms and methyl and methoxy radicals; and X may be chosen from phenyl radicals linked to the groups $CR_3R_4$ via bonds in position 1,4 relative to each other; a is equal to 1; $R_1$ and $R_2$, which are identical, are chosen from methyl radicals and ethyl radicals, and are different, and may be chosen from ethyl radicals and ethyl radicals substituted with an entity chosen from dimethylamino, trimethylammonium or benzyldimethylammonium groups; $R_5$ is chosen from a hydrogen atom; $R_6$ may be chosen from hydrogen atoms and methyl and methoxy radicals in an ortho position relative to the carbon-carbon unsaturated bond.

For example, X may be chosen from:

branched alkyl radicals comprising 4 to 14 carbon atoms;
linear and branched alkyl radicals comprising 1 to 14 carbon atoms, substituted with at least one entity chosen from halogen atoms, hetero atoms, and groups bearing at least one hetero atom; linear and branched alkyl radicals comprising 1 to 14 carbon atoms interrupted with at least one entity chosen from hetero atoms and groups comprising at least one hetero atom;
linear and branched alkene radicals comprising 2 to 14 carbon atoms, optionally interrupted with at least one entity chosen from hetero atoms and groups comprising at least one hetero atom and optionally substituted with at least one entity chosen from hetero atoms and groups bearing at least one hetero atom;

dicarbonyl radicals;

5- and 6-membered heterocyclic radicals optionally substituted with at least one entity chosen from
linear and branched alkyl radicals comprising 1 to 14 carbon atoms, optionally substituted with at least one hetero atom;
linear and branched aminoalkyl radicals, comprising 1 to 4 carbon atoms, optionally substituted with at least one hetero atom; and
halogen atoms;

$C_6$ aromatic radicals linked to the groups $CR_3R_4$ via linear or branched $C_1$-$C_4$ alkyl radicals, which may be identical or different, and comprising a group comprising at least one hetero atom which is optionally directly linked to the aromatic radical, in position 1,3 relative to each other, wherein the $C_6$ aromatic radicals are optionally substituted with at least one entity chosen from halogen atom and $C_1$-$C_4$ alkyl radicals; the; $C_6$ aromatic radicals linked to the groups $CR_3R_4$ via linear or branched $C_1$-$C_4$ alkyl radicals in position 1,2 relative to each other, which may be identical or different, and comprising a group comprising at least one hetero atom which is optionally directly linked to the aromatic radical; $C_6$ aromatic radicals linked to the groups $CR_3R_4$ via bonds in position 1,2 relative to each other, substituted with at least one group comprising at least one hetero atom; $C_6$ aromatic radicals linked to the groups $CR_3R_4$ via linear branched $C_1$-$C_4$ alkyl radicals, which may be identical or different, and containing a group comprising at least one hetero atom which may optionally be directly linked to the aromatic radical in position 1,4 relative to each other; and diphenyl radicals linked to the groups $CR_3R_4$ via bonds in position 4,4' relative to each other, the two aromatic rings optionally being linked by means of a linear or branched $C_1$-$C_4$ alkyl radical; and the group X optionally bearing at least one cationic charge.

For further example, X may be chosen from:

branched alkyl radicals comprising 4 to 13 carbon atoms; linear and branched alkyl radicals comprising 1 to 13 carbon atoms, substituted with at least one entity chosen from chlorine atoms, hydroxyl radicals, acetoxy radicals, amino radicals, and ammonium radicals; linear and branched alkyl radicals comprising 2 to 12 carbon atoms interrupted with at least one entity chosen from oxygen atoms, and nitrogen atoms comprising one or two radicals, which may be identical or different, chosen, independently of each other, from hydrogen atoms, linear and branched $C_1$-$C_4$ alkyl radicals optionally comprising a hydroxyl group; and linear and branched alkene radicals comprising 2 to 12 carbon atoms, and comprising an unsaturated carbon-carbon bond;

imidazole radicals optionally substituted with at least one $C_1$-$C_{14}$ alkyl radical;

$C_6$ aromatic radicals linked to the groups $CR_3R_4$ via linear or branched $C_1$-$C_4$ alkyl radicals, which may be identical or different, and containing a group comprising at least one hetero atom which may optionally directly linked to the aromatic radical in position 1,3 relative to each other wherein the $C_6$ aromatic radicals are optionally substituted with at least one entity chosen from fluorine atoms and methyl; $C_6$ aromatic radicals linked to the groups $CR_3R_4$ via the linear or branched $C_1$-$C_4$ alkyl radicals, which may be identical or different, and containing an amide group directly linked to the aromatic radical in position 1,4 relative to each other; and the group X optionally comprising at least one cationic charge.

In accordance with yet another aspect of the disclosure, X may be chosen from:

branched alkyl radicals comprising 4 to 13 carbon atoms; linear and branched alkyl radicals comprising 1 to 13 carbon atoms, substituted with at least one entity chosen from chlorine atoms, hydroxyl radicals, acetoxy radicals, amino radicals, and ammonium radicals; linear and branched alkyl radicals comprising 2 to 12 carbon atoms interrupted with at least one entity chosen from oxygen atoms, nitrogen atoms comprising at least one entity, which may be identical or different, chosen, independently of each other, from hydrogen atoms, and linear and branched $C_1$-$C_4$ alkyl radicals optionally comprising a hydroxyl group; and linear and branched alkene radicals comprising 2 to 12 carbon atoms, and comprising an unsaturated carbon-carbon bond;

pyridine radicals linked to the groups $CR_3R_4$ via bonds in positions 2 and 6 relative to each other;

imidazole radicals optionally substituted with at least one $C_1$-$C_{14}$ alkyl radical;

$C_6$ aromatic radicals linked to the groups $CR_3R_4$ via linear or branched $C_1$-$C_4$ alkyl radicals, which may be identical or different, and containing a group comprising at least one hetero atom which may optionally directly linked to the aromatic radical in position 1,3 relative to each other wherein the $C_6$ aromatic radicals are optionally substituted with at least one entity chosen from fluorine atoms and methyl; $C_6$ aromatic radicals linked to the groups $CR_3R_4$ via the linear or branched $C_1$-$C_4$ alkyl radicals, which may be identical or different, and containing an amide group directly linked to the aromatic radical in position 1,4 relative to each other; and the group X optionally comprising at least one cationic charge.

A further aspect of the present disclosure is a composition comprising, in a cosmetically acceptable medium, at least one fluorescent dye as provided above.

For example, the at least one fluorescent dye is present in an amount ranging from 0.01% to 20% by weight, for example, from 0.05% to 10% by weight and as such can be from 0.1% to 5% by weight, relative to the total weight of the composition.

The amount of the at least one fluorescent dye present in the composition is, such that, after application to the keratin material, such as, keratin fibers with a tone height of not more than 6, for example, not more than 4, the composition gives a reflectance, ranging from 500 to 700 nm, which may be greater than the reflectance of the untreated keratin material.

For example, the fluorescent compound is chosen from compounds having solubilities in the medium of the composition of at least 0.01 g/l, for example, at least 0.5 g/l, further for example, at least 1 g/l, and still further, at least 5 g/l, at a temperature ranging from 15° to 25° C.

The cosmetic composition used to dye keratin fibers may be in various forms, such as lotions, shampoos, creams, gels, pastes or any other suitable form.

According to one aspect of the present disclosure, the composition is in the form of a lightening dye shampoo comprising, in a cosmetically acceptable aqueous medium, at least one fluorescent compound according to the disclosure and at least one surfactant. The at least one surfactant present in the shampoo may be chosen from anionic, cationic, amphoteric and non-ionic surfactants.

As such, the at least one surfactant may, for example, be chosen from nonionic surfactants comprising alkylpolyglucosides.

In these shampoos, the surfactants are present in an amount ranging from 4% to 30% and, for example, ranging from 8% to 20% by weight, relative to the total weight of the shampoo composition.

Another aspect of the present disclosure is a multi-compartment kit comprising at least one compartment containing at least one composition comprising at least one fluorescent dye and optionally at least one entity chosen from additional fluorescent dyes, non-fluorescent direct dyes, oxidation bases, and couplers, in a cosmetically acceptable medium, and at least one other compartment containing a composition comprising at least one oxidizing agent. According to another embodiment of the kit of the disclosure, the composition comprises at least one fluorescent compound that is soluble in the medium.

The multi-compartment kit may be equipped with a means for applying the desired mixture to the hair, such as the devices described in FR 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLES

Fluorescent Compound

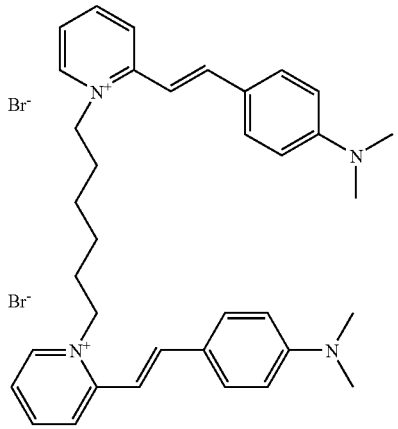

93 g of 2-picoline were reacted with 120 g of 1,6-dibromohexane in dimethylformamide at 110° C. for 5 hours.

The precipitated product was recovered and filtered off.

109 g of the product obtained above were dissolved in methanol and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C: 62.43%; H: 6.40%; Br: 23.07%; N: 8.09%.

The formula was as follows: $C_{36}H_{44}N_4 \cdot 2Br$.

Coloration on the Hair

The compound was dissolved in deionized water and the pH was adjusted to 7.1 with dilute hydrochloric acid. The concentration of the compound in the medium was 1% by weight.

The dye solution thus obtained was applied to natural hair (90% white hairs) and chestnut-brown hair (tone height 4) with a bath ratio of 5:1, for 20 minutes at room temperature.

After dyeing, the hair was rinsed with water and dried at room temperature.

Shampooing Procedures 0.4 g of Ultra Doux Camomile shampoo (Garnier) per gram of hair was applied to the predyed locks, according to the following protocol:

each lock passed 3 times between the fingers and then passed 15 times under warm water and dried for 30 minutes. Two and six shampooing cycles were performed.

Test Results

The color measurements were taken using a spectrocolorimeter (Minolta CM3600d, specular components included, illuminant D65, 10° angle).

Color Uptake on Natural Hair (90% of Natural White Hairs):

|  | L* | a* | b* |
|---|---|---|---|
| Undyed natural hair | 57.02 | 0.71 | 13.29 |
| Dyed natural hair | 47.05 | 28.12 | 42.62 |

It was found that the dye is satisfactorily taken up into the hair.

Color Uptake on Chestnut-Brown Hair:

|  | L* | a* | b* |
|---|---|---|---|
| Undyed chestnut-brown hair | 23.00 | 3.29 | 4.44 |
| Dyed chestnut-brown hair | 23.66 | 4.78 | 5.53 |

It was found that the dye is satisfactorily taken up into the hair.

Lightening Power on Natural Chestnut-Brown Hair

In FIG. 1, the simple line curve shows the reflectance obtained for the undyed chestnut-brown hair (control) and the curve marked with triangles shows the reflectance obtained for chestnut-brown hair treated in accordance with the invention.

It is found that there is a lightening effect on the hair treated according to the disclosure, compared with the undyed hair.

What is claimed is:

1. A process for dyeing human keratin materials with a lightening effect, comprising applying to the materials, a composition comprising:
   a cosmetically acceptable medium, wherein said medium is water and optionally an organic solvent and
   at least one fluorescent dye present in an amount sufficient to dye keratin materials with a lightening effect, comprised in said medium and having the following formula:

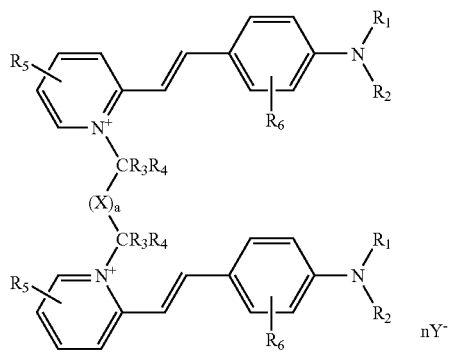

wherein:
R$_1$ and R$_2$, which may be identical or different, are chosen from:
hydrogen atoms;
linear and branched alkyl radicals comprising 1 to 10 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
aryl and arylalkyl radicals, wherein the aryl groups comprise 6 carbon atoms and the alkyl groups comprise 1 to 4 carbon atoms; the aryl groups are optionally substituted with at least one linear or branched alkyl radical comprising 1 to 4 carbon atoms optionally interrupted with at least one entity chosen from hetero atoms and groups comprising at least one hetero atom and optionally substituted with at least entity one chosen from hetero atoms, groups comprising at least one hetero atom, and halogen atoms;
R$_1$ and R$_2$ are optionally linked so as to form a heterocycle with the nitrogen atom to which they are attached and optionally further comprise at least one hetero atom, wherein the heterocycle is optionally substituted with at least one entity chosen from linear and branched alkyl radicals optionally interrupted with at least one entity chosen from hetero atoms and groups comprising at least one hetero atom and optionally substituted with at least one entity chosen from hetero atoms, groups comprising at least one hetero atom, and halogen atoms;
R$_1$ or R$_2$ is also optionally included in a heterocycle comprising the nitrogen atom to which they are attached and one of the carbon atoms of the phenyl group comprising the nitrogen atom;
R$_3$ and R$_4$, which may be identical or different, are chosen from hydrogen atoms and alkyl radicals comprising 1 to 4 carbon atoms;
R$_5$, which may be identical or different, is chosen from hydrogen atoms, halogen atoms and linear and branched alkyl radicals comprising 1 to 4 carbon atoms, optionally interrupted with at least one hetero atom;
R$_6$, which may be identical or different, is chosen from hydrogen atoms; halogen atoms;
and linear and branched alkyl radicals comprising 1 to 4 carbon atoms, optionally substituted with at least one entity chosen from hetero atoms, groups comprising at least one hetero atom and halogen atoms, and interrupted with at least one entity chosen from hetero atoms and groups comprising at least one hetero atom;
X is chosen from:
linear and branched alkyl radicals comprising 1 to 14 carbon atoms and alkenyl radicals comprising 2 to 14 carbon atoms, wherein said alkyl and alkenyl radicals are optionally interrupted with at least one entity chosen from hetero atoms and groups comprising at least one hetero atom and are optionally substituted with at least one entity chosen from hetero atoms, groups comprising at least one hetero atom, and halogen atoms;
5- and 6-membered heterocyclic radicals optionally substituted with at least one entity chosen from
linear and branched alkyl radicals comprising 1 to 14 carbon atoms, optionally substituted with at least one hetero atom;
linear and branched aminoalkyl radicals comprising 1 to 4 carbon atoms, optionally substituted with at least one hetero atom; and
halogen atoms;
fused and non-fused aromatic and diaromatic radicals, optionally separated with an alkyl radical comprising 1 to 4 carbon atoms, wherein the aromatic and diaromatic radicals are optionally substituted with at least one entity chosen from halogen atoms, and alkyl radicals comprising 1 to 10 carbon atoms optionally substituted and/or interrupted with at least one hetero atom and/or group comprising at least one hetero atom;
dicarbonyl radicals;
the group X optionally comprising at least one cationic charge;
a is equal to 0 or 1;
Y$^-$, which may be identical or different, is chosen from organic and mineral anions; and
n is an integer ranging from 2 to the number of cationic charges present in the fluorescent dye.

2. The process according to claim 1, wherein R$_1$ and R$_2$, which may be identical or different, are chosen from:
hydrogen atoms;
alkyl radicals comprising 1 to 6 carbon atoms, optionally interrupted with at least one entity chosen from oxygen atoms, and optionally substituted with at least one entity chosen from hydroxyl, amino and ammonium radicals and chlorine and fluorine atoms;
benzyl and phenyl radicals optionally substituted with at least one entity chosen from alkyl and alkoxy radicals comprising 1 to 4 carbon atoms; and
nitrogen atoms, heterocyclic radicals chosen from pyrrolo, pyrrolidino, imidazolino, imidazolo, imidazolium, pyrazolino, piperazino, morpholino, morpholo, pyrazolo and triazolo radicals, optionally substituted with at least one entity chosen from linear and branched alkyl radicals comprising 1 to 4 carbon atoms optionally interrupted with at least one entity chosen from nitrogen and oxygen atoms and groups comprising a nitrogen or oxygen atoms and optionally substituted with at least one entity chosen from nitrogen and oxygen atoms and groups comprising a nitrogen or oxygen atoms.

3. The process according to claim 1, wherein R$_1$ and R$_2$, which may be identical or different, are chosen from alkyl radicals comprising 1 to 4 carbon atoms.

4. The process according to claim 1, wherein R$_1$ and R$_2$, which may be identical or different, are chosen from methyl and ethyl radicals.

5. The process according to claim 1, wherein R$_5$ and R$_6$ are hydrogen atoms.

6. The process according to claim 1, wherein X is chosen from:
linear and branched alkyl radicals comprising 1 to 14 carbon atoms, and alkenyl radicals comprising 2 to 14 carbon atoms, optionally substituted with at least one entity chosen from oxygen and nitrogen atoms and groups comprising at least one hetero atom and optionally interrupted with at least one entity chosen from oxygen, nitrogen, and fluorine atoms, and groups comprising at least one hetero atom;
dicarbonyl radicals;
5- and 6-membered heterocyclic radicals, chosen from imidazolo, pyrazolo, triazino and pyridino radicals, optionally substituted with at least one entity chosen from linear and branched alkyl radicals comprising 1 to 14 carbon atoms; and linear and branched aminoalkyl radicals comprising 1 to 10 carbon atoms, optionally substituted with a group comprising at least one entity chosen from hetero atoms and halogen atoms; and aromatic radicals comprising 6 carbon atoms and fused and non-fused diaromatic radicals, optionally separated with at least one alkyl radical comprising 1 to 4 carbon atoms, wherein the aromatic and diaromatic radicals are optionally substituted with at least one entity chosen from halogen atoms and alkyl radicals comprising 1 to 10 carbon atoms optionally interrupted with at least one entity chosen from oxygen and nitrogen atoms, and groups comprising at least one hetero atom.

7. The process according to claim 1, wherein the at least one fluorescent dye is present in an amount ranging from 0.01% to 20% by weight, relative to the total weight of the composition.

8. The process according to claim 7, wherein the at least one fluorescent dye is present in an amount ranging from 0.05% to 10% by weight, relative to the total weight of the composition.

9. The process according to claim 8, wherein the at least one fluorescent dye is present in an amount ranging from 0.1% to 5% by weight, relative to the total weight of the composition.

10. The process according to claim 1, wherein the composition further comprises at least one additional fluorescent dye.

11. The process according to claim 10, wherein the at least one additional fluorescent dye is present in an amount ranging from 0.05% to 10% by weight relative to the total weight of the composition.

12. The process according to claim 11, wherein the at least one additional fluorescent dye is present in an amount ranging from 0.05% to 10% by weight relative to the total weight of the composition.

13. The process according to claim 1, wherein the composition further comprises at least one non-fluorescent direct dye.

14. The process according to claim 13, wherein the at least one non-fluorsecent direct dye is chosen from nitrobenzene dyes, azo dyes, azomethine dyes, methine dyes, anthraquinone dyes, naphthoquinone dyes, benzoquinone dyes, phenothiazine dyes, indigoid dyes, xanthene dyes, phenanthridine dyes, phthalocyanin dyes, and triarylmethane-based dyes.

15. The process according to claim 14, wherein the at least one direct dye is present in an amount ranging from 0.0005% to 12% by weight, relative to the total weight of the composition.

16. The process according to claim 15, wherein the at least one direct dye is present in an amount ranging from 0.005% to 6% by weight, relative to the total weight of the composition.

17. The process according to claim 1, wherein the composition further comprises at least one surfactant chosen from nonionic, anionic, cationic, amphoteric and zwitterionic surfactants.

18. The process according to claim 17, wherein the at least one surfactant is present in an amount ranging from 0.01% to 40% by weight, relative to the total weight of the composition.

19. The process according to claim 18, wherein the at least one surfactant is present in an amount ranging from 0.1% to 30% by weight, relative to the total weight of the composition.

20. The process according to claim 1, wherein the composition is in the form of a dyeing shampoo.

21. The process according to claim 1, wherein the composition is in the form of a mascara for the eyelashes or a hair mascara.

22. The process according to claim 1, wherein the composition further comprises at least one oxidation base chosen from para-phenylenediamines, bis(phenyl)alkylenediamines, para-aminophenols, ortho-aminophenols, heterocyclic bases, and the acid and alkaline agent addition salts thereof.

23. The process according to claim 22, wherein the at least one oxidation base is present in an amount ranging from 0.0005% to 12% by weight, relative to the total weight of the composition.

24. The process according to claim 23, wherein the at least one oxidation base is present in an amount ranging from 0.005% to 6% by weight, relative to the total weight of the composition.

25. The process according to claim 1, wherein the composition further comprises at least one coupler chosen from meta-phenylenediamines, meta-aminophenols, meta-diphenols, heterocyclic couplers, and the acid and alkaline agent addition salts thereof.

26. The process according to claim 25, wherein the at least one coupler is present in an amount ranging from 0.0001% to 10% by weight, relative to the total weight of the composition.

27. The process according to claim 26, wherein the at least one coupler is present in an amount ranging from 0.005% to 5% by weight, relative to the total weight of the composition.

28. The process according to claim 1, wherein the composition further comprises at least one oxidizing agent.

29. The process according to claim 28, wherein the at least one oxidizing agent is chosen from hydrogen peroxide, urea peroxide, alkali metal bromates, persalts, and enzymes.

30. The process according to claim 29, wherein the persalts are chosen from perborates and persulphates.

31. The process according to claim 29, wherein the enzymes are chosen from peroxidases and two-electron and four-electron oxidoreductases.

32. The process according to claim 1, further comprising drying the human keratin materials.

33. The process according to claim 1, further comprising:
    a) applying the composition to the human keratin materials for a time that is sufficient to develop the desired coloration and lightening,
    b) optionally rinsing the human keratin materials,
    c) optionally washing and rinsing the human keratin materials, and
    d) drying the human keratin materials.

34. The process according to claim 6, wherein the groups comprising at least one hetero atom are chosen from hydroxyl, alkoxy, amino, ammonium, amido, carbonyl, and carboxyl (—COOH— and —O—CO—) groups.

35. The process according to claim 6, wherein the linear and branched alkyl radicals comprises 1 to 10 carbon atoms.

36. The process according to claim 6, wherein the linear and branched alkyl radicals comprise 1 to 4 carbon atoms.

37. The process according to claim 6, wherein the linear and branched aminoalkyl radicals comprise 1 to 4 carbon atoms.

38. The process according to claim 6, wherein the groups comprising at least one entity chosen from hetero atoms is a hydroxyl radical.

39. The process according to claim 6, wherein the fused and non-fused diaromatic radicals comprise 10 to 12 carbon atoms.

40. A fluorescent dye having the following formula:

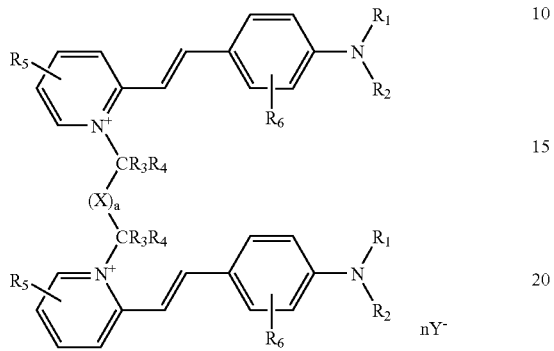

wherein:
R₁ and R₂, which may be identical or different, are chosen from:
hydrogen atoms;
linear and branched alkyl radicals comprising 1 to 10 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
aryl and arylalkyl radicals, wherein the aryl groups comprise 6 carbon atoms and the alkyl groups comprise 1 to 4 carbon atoms; the aryl groups are optionally substituted with at least one linear or branched alkyl radical comprising 1 to 4 carbon atoms optionally interrupted with at least one entity chosen from hetero atoms and groups comprising at least one hetero atom and optionally substituted with at least one entity chosen from hetero atoms, groups comprising at least one hetero atom, and halogen atoms;
R₁ and R₂ are optionally linked so as to form a heterocycle with the nitrogen atom to which they are attached and optionally comprise at least one hetero atom, wherein the heterocycle is optionally substituted with at least one entity chosen from linear and branched alkyl radicals and optionally interrupted with at least one entity chosen from hetero atoms and groups comprising at least one hetero atom and optionally substituted with at least one entity chosen from hetero atoms, groups comprising at least one hetero atom, and halogen atoms;
R₁ or R₂ is also optionally included in a heterocycle comprising the nitrogen atom and one of the carbon atoms of the phenyl group comprising the nitrogen atom;
R₃ and R₄, which may be identical or different, are chosen from hydrogen atoms and alkyl radicals comprising 1 to 4 carbon atoms;
R₅, which may be identical or different, is chosen from hydrogen atoms, halogen atoms and linear and branched alkyl radicals comprising 1 to 4 carbon atoms, optionally interrupted with at least one hetero atom;
R₆, which may be identical or different, is chosen from hydrogen atoms; halogen atoms;
and linear and branched alkyl radicals comprising 1 to 4 carbon atoms, optionally substituted with at least one entity chosen from hetero atoms, groups comprising at least one hetero atom and halogen atoms and interrupted with at least one entity chosen from hetero atoms, groups comprising at least one hetero atom, and halogen atoms;
X is chosen from:
linear and branched alkyl radicals comprising 1 to 14 carbon atoms and alkenyl radicals comprising 2 to 14 carbon atoms, wherein said alkyl and alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
5- and 6-membered heterocyclic radicals optionally substituted with at least one entity chosen from
linear and branched alkyl radicals comprising 1 to 14 carbon atoms, optionally substituted with at least one hetero atom;
linear and branched aminoalkyl radicals comprising 1 to 4 carbon atoms, optionally substituted with at least one hetero atom; and
halogen atoms;
fused and non-fused aromatic or diaromatic radicals, optionally separated with an alkyl radical comprising 1 to 4 carbon atoms, wherein the aromatic and diaromatic radicals are optionally substituted with at least one entity chosen from halogen atoms and alkyl radicals comprising 1 to 10 carbon atoms optionally substituted and/or interrupted with at least one hetero atom and/or group comprising at least one hetero atom;
dicarbonyl radicals;
the group X optionally comprising at least one cationic charge;
a is equal to 0 or 1;
Y⁻, which may be identical or different, is chosen from organic or mineral anions; and
n is an integer ranging from 2 to the number of cationic charges present in the fluorescent dye;
with the exception of the dye for which:
X is chosen from unsubstituted linear alkyl radicals comprising 1 or 4 carbon atoms wherein a is equal to 1 or a is equal to 0; and R₁ and R₂ simultaneously are methyl radicals; R₅ and R₆ are hydrogen atoms; R₃ and R₄, which may be identical, are hydrogen atoms;
X is chosen from ethyl, linear and branched unsubstituted C₃ alkyl radicals, wherein a is equal to 1; R₃ and R₄, which are identical, are hydrogen atoms; R₅ is a hydrogen atom; wherein R₁ and R₂:
are identical, and are methyl radicals and, R₆ is chosen from a hydrogen atom and a methyl radical in an ortho position relative to the carbon atom of the benzene ring bearing the carbon-carbon unsaturated bond; and
are identical, are ethyl radicals,
and R₆ is chosen from hydrogen atoms and methoxy radicals in an ortho position relative to the carbon atom of the benzene ring bearing the carbon-carbon unsaturated bond; or are different, and are chosen from ethyl radicals and ethyl radicals substituted with an entity chosen from dimethylamino, trimethylammonium and benzyldimethylammonium groups;

X is chosen from phenyl radicals linked to the groups $CR_3R_4$ via bonds in the 1,4 position relative to each other; $R_3$ and $R_4$, which are identical, are hydrogen atoms; wherein a is equal to 1; $R_5$ is a hydrogen atom; wherein $R_1$ and $R_2$:

are identical, and are methyl radicals, $R_6$ is chosen from hydrogen atoms and methyl radicals in an ortho position relative to the carbon atom of the benzene ring bearing the carbon-carbon unsaturated bond;

and are identical, comprise ethyl radicals, and $R_6$ is chosen from hydrogen atoms and methoxy radicals in an ortho position relative to the carbon atom of the benzene ring bearing the carbon-carbon unsaturated bond; or are different, and are chosen from ethyl radicals and ethyl radicals substituted with an entity chosen from dimethylamino, trimethylammonium and benzyldimethylammonium groups.

41. The dye of claim 40, wherein $R_1$ and $R_2$, which may be identical or different, are chosen from:

hydrogen atoms;

alkyl radicals comprising 1 to 6 carbon atoms, optionally interrupted with an oxygen atom and optionally substituted with at least one entity chosen from hydroxyl, amino and ammonium radicals and chlorine and fluorine atoms;

benzyl and phenyl radicals optionally substituted with at least one entity chosen from alkyl and alkoxy radicals comprising 1 to 4 carbon atoms;

nitrogen atoms, heterocyclic radicals chosen from pyrrolo, pyrrolidino, imidazolino, imidazolo, imidazolium, pyrazolino, piperazino, morpholino, morpholo, pyrazolo and triazolo radicals, optionally substituted with at least one entity chosen from linear and branched alkyl radicals comprising 1 to 4 carbon atoms optionally interrupted with at least one entity chosen from nitrogen and oxygen atom, and groups comprising a nitrogen or oxygen atoms, and optionally substituted with at least one entity chosen from nitrogen and oxygen atoms and groups comprising nitrogen and/or oxygen atoms.

42. The dye according to claim 41, wherein the alkyl and alkoxy radicals comprise 1 or 2 carbon atoms.

43. The dye according to claim 40, wherein $R_1$ and $R_2$, which may be identical or different, are chosen from alkyl radicals comprising 1 to 4 carbon atoms.

44. The dye according to claim 43, wherein $R_1$ and $R_2$, which may be identical or different, are chosen from methyl radicals and ethyl radicals.

45. The dye according to claim 40, wherein $R_5$ and $R_6$ are hydrogen atoms.

46. The dye according to claim 40, wherein X is chosen from:

branched alkyl radicals comprising 4 to 14 carbon atoms; linear and branched alkyl radicals comprising 1 to 14 carbon atoms, substituted with at least one entity chosen from halogen atoms, hetero atoms, and groups bearing at least one hetero atom; linear and branched alkyl radicals comprising 1 to 14 carbon atoms interrupted with at least one entity chosen from hetero atoms and groups comprising at least one hetero atom;

linear and branched alklene radicals comprising 2 to 14 carbon atoms, optionally interrupted with at least one entity chosen from hetero atoms and groups comprising at least one hetero atom and optionally substituted with at least one entity chosen from hetero atoms and groups bearing at least one hetero atom;

dicarbonyl radicals;

5- and 6-membered heterocyclic radicals optionally substituted with at least one entity chosen from alkyl radicals comprising 1 to 14 carbon atoms, optionally substituted with at least one hetero atom; linear and branched aminoalkyl radicals, comprising 1 to 4 carbon atoms, optionally substituted with at least one hetero atom; and halogen atoms;

$C_6$ aromatic radicals linked to the groups $CR_3R_4$ via linear or branched $C_1$-$C_4$ alkyl radicals, which may be identical or different, and comprising a group comprising at least one hetero atom which is optionally directly linked to the aromatic radical, in position 1,3 relative to each other, wherein the $C_6$ aromatic radicals are optionally substituted with at least one entity chosen from halogen atom and $C_1$-$C_4$ alkyl radicals; the; $C_6$ aromatic radicals linked to the groups $CR_3R_4$ via, linear or branched $C_1$-$C_4$ alkyl radicals in position 1,2 relative to each other, which may be identical or different, and comprising a group comprising at least one hetero atom which isoptionally directly linked to the aromatic radical; $C_6$ aromatic radicals linked to the groups $CR_3R_4$ via bonds in position 1,2 relative to each other, substituted with at least one group comprising at least one hetero atom; $C_6$ aromatic radicals linked to the groups $CR_3R_4$ via linear branched $C_1$-$C_4$ alkyl radicals, which may be identical or different, and containing a group comprising at least one hetero atom which may optionally be directly linked to the aromatic radical in position 1,4 relative to each other; and diphenyl radicals linked to the groups $CR_3R_4$ via bonds in position 4,4' relative to each other, the two aromatic rings optionally being linked by means of a linear or branched $C_1$-$C_4$ alkyl radical; and the group X optionally bearing at least one cationic charge.

47. The dye according to claim 40, wherein X is chosen from:

branched alkyl radicals comprising 4 to 13 carbon atoms; linear and branched alkyl radicals comprising 1 to 13 carbon atoms, substituted with at least one entity chosen from chlorine atoms, hydroxyl radicals acetoxy radicals, amino radicals, and ammonium radicals; linear and branched alkyl radicals comprising 2 to 12 carbon atoms interrupted with at least one entity chosen from oxygen atoms, nitrogen atoms comprising at least one entity, which may be identical or different, chosen, independently of each other, from hydrogen atoms, and linear and branched $C_1$-$C_4$ alkyl radicals optionally comprising a hydroxyl group; and linear and branched alkene radicals comprising 2 to 12 carbon atoms, and comprising an unsaturated carbon-carbon bond;

pyridine radicals linked to the groups $CR_3R_4$ via bonds in positions 2 and 6 relative to each other;

imidazole radicals optionally substituted with at least one $C_1$-$C_{14}$ alkyl radical;

$C_6$ aromatic radicals linked to the groups $CR_3R_4$ via linear and branched $C_1$-$C_4$ alkyl radicals, which may be identical or different, and containing a group comprising at least one hetero atom which may optionally be directly linked to the aromatic radical in position 1,3 relative to each other wherein the $C_6$ aromatic radicals are optionally substituted with at least one entity chosen from fluorine atoms and methyl; the bonds comprising $C_6$ aromatic radicals linked to the groups $CR_3R_4$ via linear or branched $C_1$-$C_4$ alkyl radicals, which may be identical or different, and containing a group comprising an oxygen atom directly linked to the aromatic radical in position 1,2 relative to each other; $C_6$ aromatic radicals linked to the groups $CR_3R_4$ via bonds in position 1,2 relative to each other, substituted with at least one-C(=O)O—; $C_6$ aromatic radicals linked to the groups $CR_3R_4$ via linear or branched $C_1$-$C_4$ alkyl radicals, which may be identical or different, and comprising at least one amide group directly linked to the aromatic radical in position 1,4 relative to each other; and diphenyl radicals linked to the groups $CR_3R_4$ via bonds in position 4,4' relative to each other, the two aromatic rings being optionally linked by a linear or branched alkyl radical containing 1 to 4 carbon atoms;

the group X optionally comprising at least one cationic charge.

48. The dye according to claim 40, wherein X is chosen from:

branched alkyl radicals comprising 4 to 13 carbon atoms; linear and branched alkyl radicals comprising 1 to 13 carbon atoms, substituted with at least one entity chosen from chlorine atoms, hydroxyl radicals, acetoxy radicals, amino radicals, and ammonium radicals; linear and branched alkyl radicals comprising 2 to 12 carbon atoms interrupted with at least one entity chosen from oxygen atoms, and nitrogen atoms comprising one or two radicals, which may be identical or different, chosen, independently of each other, from hydrogen atoms, linear and branched $C_1$-$C_4$ alkyl radicals optionally comprising a hydroxyl group; and linear and branched alkene radicals comprising 2 to 12 carbon atoms, and comprising an unsaturated carbon-carbon bond;

imidazole radicals optionally substituted with at least one $C_1$-$C_{14}$ alkyl radical;

$C_6$ aromatic radicals linked to the groups $CR_3R_4$ via linear or branched $C_1$-$C_4$ alkyl radicals, which may be identical or different, and containing a group comprising at least one hetero atom which may optionally be directly linked to the aromatic radical in position 1,3 relative to each other wherein the $C_6$ aromatic radicals are optionally substituted with at least one entity chosen from fluorine atoms and methyl; $C_6$ aromatic radicals linked to the groups $CR_3R_4$ via the linear or branched $C_1$-$C_4$ alkyl radicals, which may be identical or different, and containing an amide group directly linked to the aromatic radical in position 1,4 relative to each other; and the group X optionally comprising at least one cationic charge.

49. The dye according to claim 40, wherein:

$R_1$ and $R_2$, which may be identical or different, are chosen from methyl radicals and ethyl radicals, $R_5$ and $R_6$ comprise hydrogen atoms, X is chosen from:

branched alkyl radicals comprising 4 to 13 carbon atoms; linear or branched alkyl radicals comprising 1 to 13 carbon atoms, substituted with at least one entity chosen from chlorine atoms, hydroxyl radicals, acetoxy radicals, amino radicals, and ammonium radicals; linear and branched alkyl radicals comprising 2 to 12 carbon atoms interrupted with at least one entity chosen from oxygen atoms, and nitrogen atoms comprising at least one radical, which may be identical or different, chosen, independently of each other, from hydrogen atoms, and linear and branched $C_1$-$C_4$ alkyl radicals optionally comprising a hydroxyl group; linear and branched alkene radicals comprising 2 to 12 carbon atoms, and comprising an unsaturated carbon-carbon bond;

imidazole radicals optionally substituted with at least one $C_1$-$C_{14}$ alkyl radical;

$C_6$ aromatic radicals linked to the groups $CR_3R_4$ via linear and branched $C_1$-$C_4$ alkyl radicals, which may be identical or different, and containing a group comprising at least one hetero atom which is optionally directly linked to the aromatic radical in position 1,3 relative to each other wherein the $C_6$ aromatic radicals are optionally substituted with at least one entity chosen from fluorine atoms and methyl; ; $C_6$ aromatic radicals linked to the groups $CR_3R_4$ via linear and branched $C_1$-$C_4$ alkyl radicals, which may be identical or different, and containing an amide group directly linked to the aromatic radical in position 1,4, relative to each other; and the group X optionally comprising at least one cationic charge.

50. A composition comprising:

a cosmetically acceptable medium, wherein said medium is water and optionally an organic solvent and at least one fluorescent dye present in an amount sufficient to dye keratin materials with a lightening effect, comprised in said medium and having the following formula:

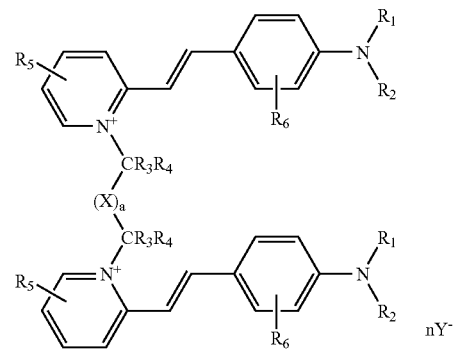

wherein:

$R_1$ and $R_2$, which may be identical or different, are chosen from:

hydrogen atoms;

linear and branched alkyl radicals comprising 1to 10 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

aryl and arylalkyl radicals, wherein the aryl groups comprising 6 carbon atoms and the alkyl groups comprise 1 to 4 carbon atoms; the aryl groups optionally be substituted with at least one linear or branched alkyl radicals comprising 1 to 4 carbon atoms optionally interrupted with at least one entity chosen from hetero atoms and groups comprising at least one hetero atom and optionally substituted with at least entity chosen from one hetero atoms, groups comprising at least one hetero atom, and halogen atoms;

$R_1$ and $R_2$ is optionally linked so as to form a heterocycle with the nitrogen atom and optionally further comprises at least one hetero atom, wherein the heterocycle is optionally substituted with at least one entity chosen from linear and branched alkyl radicals optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ or $R_2$ is also optionally included in a heterocycle comprising the nitrogen atom and one of the carbon atoms of the phenyl group comprising the nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms and linear and branched alkyl radicals comprising 1 to 4 carbon atoms, optionally interrupted with at least one hetero atom;

$R_6$, which may be identical or different, is chosen from hydrogen atoms; halogen atoms;

and linear and branched alkyl radicals comprising 1 to 4 carbon atoms, optionally substituted with at least one entity chosen from hetero atoms, groups comprising at least one hetero atom and halogen atoms, and interrupted with at least one entity chosen from hetero atoms and groups comprising at least one hetero atom;

X is chosen from:
  linear and branched alkyl radicals comprising 1 to 14 carbon atoms and alkenyl radicals comprising 2 to 14 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
  5- and 6-membered heterocyclic radicals optionally substituted with at least one entity chosen from linear and branched alkyl radicals comprising 1 to 14 carbon atoms, optionally substituted with at least one hetero atom
  linear and branched aminoalkyl radicals comprising 1 to 4 carbon atoms, optionally substituted with at least one hetero atom; and halogen atoms;
  fused and non-fused aromatic and diaromatic radicals, optionally separated with an alkyl radical comprising 1 to 4 carbon atoms, wherein the aromatic and diaromatic radicals are optionally substituted with at least one entity chosen from halogen atoms, and alkyl radicals comprising 1 to 10 carbon atoms optionally substituted and/or interrupted with at least one hetero atom and/or group comprising at least one hetero atom;
  dicarbonyl radicals;
  the group X optionally comprising at least one cationic charge;

a is equal to 0 or 1;

$Y^-$, which may be identical or different, is chosen from organic and mineral anions; and n is an integer ranging from 2 to the number of cationic charges present in the fluorescent dye.

51. The composition according to claim 50, wherein $R_1$ and $R_2$, which may be identical or different, are chosen from:
  hydrogen atoms;
  alkyl radicals comprising 1 to 6 carbon atoms, optionally interrupted with at least one entity chosen from oxygen atoms, and optionally substituted with at least one entity chosen from hydroxyl, amino and ammonium radicals and chlorine and fluorine atoms;
  benzyl and phenyl radicals optionally substituted with at least one entity chosen from alkyl and alkoxy radicals comprising 1 to 4 carbon atoms; and
  nitrogen atoms, heterocyclic radicals chosen from pyrrolo, pyrrolidino, imidazolino, imidazolo, imidazolium, pyrazolino, piperazino, morpholino, morpholo, pyrazolo and triazolo radicals, optionally substituted with at least one entity chosen from linear and branched alkyl radicals comprising 1 to 4 carbon atoms optionally interrupted with at least one entity chosen from nitrogen and oxygen atoms and groups comprising a nitrogen or oxygen atoms and optionally substituted with at least one entity chosen from nitrogen and oxygen atoms and groups comprising a nitrogen or oxygen atoms.

52. The composition according to claim 50, wherein $R_1$ and $R_2$, which may be identical or different, are chosen from alkyl radicals comprising 1 to 4 carbon atoms.

53. The composition according to claim 50, wherein $R_1$ and $R_2$, which may be identical or different, are chosen from methyl and ethyl radicals.

54. The composition according to claim 50, wherein $R_5$ and $R_6$ are hydrogen atoms.

55. The composition according to claim 50, wherein X is chosen from:
  linear and branched alkyl radicals comprising 1 to 14 carbon atoms, and alkenyl radicals comprising 2 to 14 carbon atoms, optionally substituted with at least one entity chosen from oxygen and nitrogen atoms and groups comprising at least one hetero atom and optionally interrupted with at least one entity chosen from oxygen nitrogen, and fluorine atoms, and groups comprising at least one hetero atom
  dicarbonyl radicals;
  5- and 6-membered heterocyclic radicals, chosen from imidazolo, pyrazolo, triazino and pyridino radicals, optionally substituted with at least one entity chosen from linear and branched alkyl radicals comprising 1 to 14 carbon atoms; and linear and branched aminoalkyl radicals comprising 1 to 10 carbon atoms, optionally substituted with a group comprising at least one entity chosen from hetero atoms and halogen atoms; and
  aromatic radicals comprising 6 carbon atoms and fused and non-fused diaromatic radicals, optionally separated with at least one alkyl radical comprising 1 to 4 carbon atoms, wherein the aromatic and diaromatic radicals are optionally substituted with at least one entity chosen from halogen atoms and alkyl radicals comprising 1 to 10 carbon atoms optionally interrupted with at least one entity chosen from oxygen and nitrogen atoms, and groups comprising at least one hetero atom.

56. The composition according to claim 50, wherein the at least one fluorescent dye is present in an amount ranging from 0.01% to 20% by weight, relative to the total weight of the composition.

57. The composition according to claim 50, wherein the at least one fluorescent dye is present in an amount ranging from 0.05% to 10% by weight, relative to the total weight of the composition.

58. The composition according to claim 57, wherein the at least one fluorescent dye is present in an amount ranging from 0.1% to 5% by weight, relative to the total weight of the composition.

59. The composition according to claim 50, wherein the composition further comprises at least one additional fluorescent dye.

60. The composition according to claim 59, wherein the at least one additional fluorescent dye is present in an amount ranging from 0.05% to 10% by weight relative to the total weight of the composition.

61. The composition according to claim 60, wherein the at least one additional fluorescent dye is present in an amount ranging from 0.05% to 10% by weight, relative to the total weight of the composition.

62. The composition according to claim 50, wherein the composition further comprises at least one non-fluorescent direct dye.

63. The composition according to claim 62, wherein the at least one non-fluorescent direct dye is chosen from nitrobenzene dyes, azo dyes, azomethine dyes, methane dyes, anthraquinone dyes, naphthoquinone dyes, benzoquinone dyes, phenothiazine dyes, indigoid dyes, xanthene dyes, phenanthridine dyes, phthalocyanin dyes, and triarylmethane-based dyes.

64. The composition according to claim 63, wherein the at least one direct dye is present in an amount ranging from 0.0005% to 12% by weight, relative to the total weight of the composition.

65. The composition according to claim 64, wherein the at least one direct dye is present in an amount ranging from 0.005% to 6% by weight, relative to the total weight of the composition.

66. The composition according to claim 50, wherein the composition further comprises at least one surfactant chosen from nonionic, anionic, cationic, amphoteric and zwitterionic surfactants.

67. The composition according to claim 66, wherein the at least one surfactant is present in an amount ranging from 0.01% to 40% by weight, relative to the total weight of the composition.

68. The composition according to claim 67, wherein the at least one surfactant is present in an amount ranging from 0.1% to 30% by weight, relative to the total weight of the composition.

69. The composition according to claim 50, wherein the composition is in the form of a dyeing shampoo.

70. The composition according to claim 50, wherein the composition is in the form of a mascara for the eyelashes or a hair mascara.

71. The composition according to claim 50, wherein the composition further comprises at least one oxidation base chosen from para-phenylenediamines, bis(phenyl)alkylenediamines, para-aminophenols, ortho-aminophenols, heterocyclic bases, and the acid and alkaline agent addition salts thereof.

72. The composition according to claim 71, wherein the at least one oxidation base is present in an amount ranging from 0.0005% to 12% by weight, relative to the total weight of the composition.

73. The composition according to claim 72, wherein the at least one oxidation base is present in an amount ranging from 0.005% to 6% by weight, relative to the total weight of the composition.

74. The composition according to claim 50, wherein the composition further comprises at least one coupler chosen from meta-phenylenediamines, meta-aminophenols, meta-diphenols, heterocyclic couplers, and the acid and alkaline agent addition salts thereof.

75. The composition according to claim 74, wherein the at least one coupler is present in an amount ranging from 0.0001% to 10% by weight, relative to the total weight of the composition.

76. The composition according to claim 75, wherein the at least one coupler is present in an amount ranging from 0.005% to 5% by weight, relative to the total weight of the composition.

77. The composition according to claim 50, wherein the composition further comprises at least one oxidizing agent.

78. The composition according to claim 77, wherein the at least one oxidizing agent is chosen from hydrogen peroxide, urea peroxide, alkali metal bromates, persalts, and enzymes.

79. The composition according to claim 78, wherein the persalts are chosen from perborates and persulphates.

80. The composition according to claim 78, wherein the enzymes are chosen from peroxidases and two-electron and four-electron oxidoreductases.

81. The composition according to claim 55, wherein the groups comprising at least one hetero atom are chosen from hydroxyl, alkoxy, amino, ammonium, amido, carbonyl, and carboxyl (—COOH— and —O—CO—) groups.

82. The composition according to claim 6, wherein the linear and branched alkyl radicals comprises 1 to 10 carbon atoms.

83. The composition according to claim 55, wherein the linear and branched alkyl radicals comprise 1 to 4 carbon atoms.

84. The composition according to claim 55, wherein the linear and branched aminoalkyl radicals comprise 1 to 4 carbon atoms.

85. The composition according to claim 55, wherein the groups comprising at least one entity chosen from hetero atoms is a hydroxyl radical.

86. The composition according to claim 55, wherein the fused and non-fused diaromatic radicals comprise 10 to 12 carbon atoms.

87. A composition comprising, in a cosmetically acceptable medium, at least one fluorescent dye having the following formula:

wherein:
R₁ and R₂, which may be identical or different, are chosen from:
  hydrogen atoms;
  linear and branched alkyl radicals comprising 1 to 10 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
  aryl and arylalkyl radicals, wherein the aryl groups comprising 6 carbon atoms and the alkyl groups comprise 1 to 4 carbon atoms; the aryl groups optionally be substituted with at least one linear or branched alkyl radicals comprising 1 to 4 carbon atoms optionally interrupted with at least one entity chosen from hetero atoms and groups comprising at least one hetero atom and optionally substituted with at least entity chosen from one hetero atoms, groups comprising at least one hetero atom, and halogen atoms;
  $R_1$ and $R_2$ is optionally linked so as to form a heterocycle with the nitrogen atom and optionally further comprises at least one hetero atom, wherein the heterocycle is optionally substituted with at least one entity chosen from linear and branched alkyl radicals optionally interrupted with at least one entity chosen from hetero atoms and groups comprising at least one hetero atom and optionally substituted with at least one entity chosen from hetero atoms, groups comprising at least one hetero atom, and halogen atoms;
  $R_1$ or $R_2$ is also optionally included in a heterocycle comprising the nitrogen atom and one of the carbon atoms of the phenyl group comprising the nitrogen atom;
$R_3$ and $R_4$, which may be identical or different, are chosen from hydrogen atoms and alkyl radicals comprising 1 to 4 carbon atoms;
$R_5$, which may be identical or different, is chosen from hydrogen atoms, halogen atoms and linear and branched alkyl radicals comprising 1 to 4 carbon atoms, optionally interrupted with at least one hetero atom;
$R_6$, which may be identical or different, is chosen from hydrogen atoms; halogen atoms; and linear and branched alkyl radicals comprising 1 to 4 carbon atoms, optionally substituted with at least one entity chosen from hetero atoms, groups comprising at least one hetero atom and halogen atoms, and interrupted with at least one entity chosen from hetero atoms and groups comprising at least one hetero atom;
X is chosen from:
  linear and branched alkyl radicals comprising 1 to 14 carbon atoms and alkenyl radicals comprising 2 to 14 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
  5- and 6-membered heterocyclic radicals optionally substituted with at least one entity chosen from linear and branched alkyl radicals comprising 1 to 14 carbon atoms, optionally substituted with at least one hetero atom; linear and branched aminoalkyl radicals comprising 1 to 4 carbon atoms, optionally substituted with at least one hetero atom; and halogen atoms;
  fused and non-fused aromatic and diaromatic radicals, optionally separated with an alkyl radical comprising 1 to 4 carbon atoms, wherein the aromatic and diaromatic radicals are optionally substituted with at least one entity chosen from halogen atoms, and alkyl radicals comprising 1 to 10 carbon atoms optionally substituted and/or interrupted with at least one hetero atom and/or group comprising at least one hetero atom;
  dicarbonyl radicals;
  the group X optionally comprising at least one cationic charge;
a is equal to 0 or 1;
$Y^-$, which may be identical or different, is chosen from organic and mineral anions; and
  n is an integer ranging from 2 to the number of cationic charges present in the fluorescent dye;
with the exception of the dye for which:
  X is chosen from unsubstituted linear alkyl radicals comprising 1 or 4 carbon atoms wherein a is equal to 1 or a is equal to 0; and $R_1$ and $R_2$ simultaneously are methyl radicals; $R_5$ and $R_6$ are hydrogen atoms; $R_3$ and $R_4$, which may be identical, are hydrogen atoms;
  X is chosen from ethyl, linear and branched unsubstituted $C_3$ alkyl radicals, wherein a is equal to 1; $R_3$ and $R_4$, which are identical, are hydrogen atoms; $R_5$ is a hydrogen atom; wherein $R_1$ and $R_2$:
    are identical, and are methyl radicals and, $R_6$ is chosen from a hydrogen atom and a methyl radical in an ortho position relative to the carbon atom of the benzene ring bearing the carbon-carbon unsaturated bond; and
    are identical, are ethyl radicals,
    and $R_6$ is chosen from hydrogen atoms and methoxy radicals in an ortho position relative to the carbon atom of the benzene ring bearing the carbon-carbon unsaturated bond; or
    are different, and are chosen from ethyl radicals and ethyl radicals substituted with an entity chosen from dimethylamino, trimethylammonium and benzyldimethylammonium groups;
  X is chosen from phenyl radicals linked to the groups $CR_3R_4$ via bonds in the 1,4 position relative to each other; $R_3$ and $R_4$, which are identical, are hydrogen atoms; wherein a is equal to 1; $R_5$ is a hydrogen atom; wherein $R_1$ and $R_2$:
    are identical, and are methyl radicals, $R_6$ is chosen from hydrogen atoms and methyl radicals in an ortho position relative to the carbon atom of the benzene ring bearing the carbon-carbon unsaturated bond;
    and are identical, comprise ethyl radicals, and $R_6$ is chosen from hydrogen atoms and methoxy radicals in an ortho position relative to the carbon atom of the benzene ring bearing the carbon-carbon unsaturated bond; or
    are different, and are chosen from ethyl radicals and ethyl radicals substituted with an entity chosen from dimethylamino, trimethylammonium and benzyldimethylammonium groups.

88. The composition of claim 87, wherein $R_1$ and $R_2$, which may be identical or different, are chosen from:

hydrogen atoms;
alkyl radicals comprising 1 to 6 carbon atoms, optionally interrupted with an oxygen atom and optionally substituted with at least one entity chosen from hydroxyl, amino and ammonium radicals and chlorine and fluorine atoms;
benzyl and phenyl radicals optionally substituted with at least one entity chosen from alkyl and alkoxy radicals comprising 1 to 4 carbon atoms;
nitrogen atoms, heterocyclic radicals chosen from pyrrolo, pyrrolidino, imidazolino, imidazolo, imidazolium, pyrazolino, piperazino, morpholino, morpholo, pyrazolo and triazolo radicals, optionally substituted with at least one entity chosen from linear and branched alkyl radicals comprising 1 to 4 carbon atoms optionally interrupted with at least one entity chosen from nitrogen and oxygen atom, and groups comprising a nitrogen or oxygen atoms, and optionally substituted with at least one entity chosen from nitrogen and oxygen atoms and groups comprising nitrogen and/or oxygen atoms.

89. The composition according to claim 88, wherein the alkyl and alkoxy radical comprises 1 or 2 carbon atoms.

90. The composition according to claim 87, wherein $R_1$ and $R_2$, which may be identical or different, are chosen from alkyl radicals comprising 1 to 4 carbon atoms.

91. The composition according to claim 90, wherein $R_1$ and $R_2$, which may be identical or different, are chosen from methyl radicals and ethyl radicals.

92. The composition according to claim 87, wherein $R_5$ and $R_6$ are hydrogen atoms.

93. The composition according to claim 87, wherein X is chosen from:
branched alkyl radicals comprising 4 to 14 carbon atoms; linear and branched alkyl radicals comprising 1 to 14 carbon atoms, substituted with at least one entity chosen from halogen atoms, hetero atoms, and groups bearing at least one hetero atom;
linear and branched alkyl radicals comprising 1 to 14 carbon atoms interrupted with at least one entity chosen from hetero atoms and groups comprising at least one hetero atom; linear and branched alkenyl radicals comprising 2 to 14 carbon atoms, optionally interrupted with at least one entity chosen from hetero atoms and groups comprising at least one hetero atom and optionally substituted with at least one entity chosen from hetero atoms and groups bearing at least one hetero atom;
dicarbonyl radicals;
5- and 6-membered heterocyclic radicals optionally substituted with at least one entity chosen from alkyl radicals comprising 1 to 14 carbon atoms, optionally substituted with at least one hetero atom; linear and branched aminoalkyl radicals, comprising 1 to 4 carbon atoms, optionally substituted with at least one hetero atom; and halogen atoms;
$C_6$ aromatic radicals linked to the groups $CR_3R_4$ via linear or branched $C_1$-$C_4$ alkyl radicals, which may be identical or different, and comprising a group comprising at least one hetero atom which is optionally directly linked to the aromatic radical, in position 1,3 relative to each other, wherein the $C_6$ aromatic radicals are optionally substituted with at least one entity chosen from halogen atom and $C_1$-$C_4$ alkyl radicals; $C_6$ aromatic radicals linked to the groups $CR_3R_4$ via, linear or branched $C_1$-$C_4$ alkyl radicals in position 1,2 relative to each other, which may be identical or different, and comprising a group comprising at least one hetero atom which isoptionally directly linked to the aromatic radical; $C_6$ aromatic radicals linked to the groups $CR_3R_4$ via bonds in position 1,2 relative to each other, substituted with at least one group comprising at least one hetero atom; $C_6$ aromatic radicals linked to the groups $CR_3R_4$ via linear branched $C_1$-$C_4$ alkyl radicals, which may be identical or different, and containing a group comprising at least one hetero atom which may optionally be directly linked to the aromatic radical in position 1,4 relative to each other; and diphenyl radicals linked to the groups $CR_3R_4$ via bonds in position 4,4' relative to each other, the two aromatic rings optionally being linked by means of a linear or branched $C_1$-$C_4$ alkyl radical; and
the group X optionally bearing at least one cationic charge.

94. The composition according to claim 87, wherein X is chosen from:
branched alkyl radicals comprising 4 to 13 carbon atoms; linear and branched alkyl radicals comprising 1 to 13 carbon atoms, substituted with at least one entity chosen from chlorine atoms, hydroxyl radicals acetoxy radicals, amino radicals, and ammonium radicals; linear and branched alkyl radicals comprising 2 to 12 carbon atoms interrupted with at least one entity chosen from oxygen atoms, nitrogen atoms comprising at least one entity, which may be identical or different, chosen, independently of each other, from hydrogen atoms, and linear and branched $C_1$-$C_4$ alkyl radicals optionally comprising a hydroxyl group; and linear and branched alkene radicals comprising 2 to 12 carbon atoms, and comprising an unsaturated carbon-carbon bond;
pyridine radicals linked to the groups $CR_3R_4$ via bonds in positions 2 and 6 relative to each other;
imidazole radicals optionally substituted with at least one $C_1$-$C_{14}$ alkyl radical;
$C_6$ aromatic radicals linked to the groups $CR_3R_4$ via linear and branched $C_1$-$C_4$ alkyl radicals, which may be identical or different, and containing a group comprising at least one hetero atom which may optionally be directly linked to the aromatic radical in position 1,3 relative to each other wherein the $C_6$ aromatic radicals are optionally substituted with at least one entity chosen from fluorine atoms and methyl; the bonds comprising $C_6$ aromatic radicals linked to the groups $CR_3R_4$ via linear or branched $C_1$-$C_4$ alkyl radicals, which may be identical or different, and containing a group comprising an oxygen atom directly linked to the aromatic radical in position 1,2 relative to each other; $C_6$ aromatic radicals linked to the groups $CR_3R_4$ via bonds in position 1,2 relative to each other, substituted with at least one-C(=O)O—; $C_6$ aromatic radicals linked to the groups $CR_3R_4$ via linear or branched $C_1$-$C_4$ alkyl radicals, which may be identical or different, and comprising at least one amide group directly linked to the aromatic radical in position 1,4 relative to each other; and diphenyl radicals linked to the groups $CR_3R_4$ via bonds in position 4,4' relative to each other, the two aromatic rings being optionally linked by a linear or branched alkyl radical containing 1 to 4 carbon atoms;
the group X optionally comprising at least one cationic charge.

95. The composition according to claim 87, wherein X is chosen from:
branched alkyl radicals comprising 4 to 13 carbon atoms; linear and branched alkyl radicals comprising 1 to 13 carbon atoms, substituted with at least one entity chosen from chlorine atoms, hydroxyl radicals, acetoxy radicals, amino radicals, and ammonium radicals; linear and branched alkyl radicals comprising 2 to 12 carbon atoms interrupted with at least one entity chosen from oxygen atoms, and nitrogen atoms comprising one or two radicals, which may be identical or different, chosen, independently of each other, from hydrogen atoms, linear and branched $C_1$-$C_4$ alkyl radicals optionally comprising a hydroxyl group; and linear and branched alkene radicals comprising 2 to 12 carbon atoms, and comprising an unsaturated carbon-carbon bond;

imidazole radicals optionally substituted with at least one $C_1$-$C_{14}$ alkyl radical;

$C_6$ aromatic radicals linked to the groups $CR_3R_4$ via linear or branched $C_1$-$C_4$ alkyl radicals, which may be identical or different, and containing a group comprising at least one hetero atom which may optionally directly linked to the aromatic radical in position 1,3 relative to each other wherein the $C_6$ aromatic radicals are optionally substituted with at least one entity chosen from fluorine atoms and methyl; $C_6$ aromatic radicals linked to the groups $CR_3R_4$ via the linear or branched $C_1$-$C_4$ alkyl radicals, which may be identical or different, and containing an amide group directly linked to the aromatic radical in position 1,4 relative to each other; and the group X optionally comprising at least one cationic charge.

96. The composition according to claim 87, wherein:

$R_1$ and $R_2$, which may be identical or different, are chosen from methyl radicals and ethyl radicals, $R_5$ and $R_6$ comprise hydrogen atoms, X is chosen from:
branched alkyl radicals comprising 4 to 13 carbon atoms; linear or branched alkyl radicals comprising 1 to 13 carbon atoms, substituted with at least one entity chosen from chlorine atoms, hydroxyl radicals, acetoxy radicals, amino radicals, and ammonium radicals; linear and branched alkyl radicals comprising 2 to 12 carbon atoms interrupted with at least one entity chosen from oxygen atoms, and nitrogen atoms comprising at least one radical, which may be identical or different, chosen, independently of each other, from hydrogen atoms, and linear and branched $C_1$-$C_4$ alkyl radicals optionally comprising a hydroxyl group; linear and branched alkene radicals comprising 2 to 12 carbon atoms, and comprising an unsaturated carbon-carbon bond;

imidazole radicals optionally substituted with at least one $C_1$-$C_{14}$ alkyl radical;

$C_6$ aromatic radicals linked to the groups $CR_3R_4$ via linear and branched $C_1$-$C_4$ alkyl radicals, which may be identical or different, and containing a group comprising at least one hetero atom which is optionally directly linked to the aromatic radical in position 1,3 relative to each other wherein the $C_6$ aromatic radicals are optionally substituted with at least one entity chosen from fluorine atoms and methyl; ; $C_6$ aromatic radicals linked to the groups $CR_3R_4$ via linear and branched $C_1$-$C_4$ alkyl radicals, which may be identical or different, and containing an amide group directly linked to the aromatic radical in position 1,4, relative to each other; and the group X optionally comprising at least one cationic charge.

97. A multi-kit comprising a first compartment comprising at least one composition, the composition comprises, in a cosmetically acceptable medium, at least one fluorescent dye having the following formula:

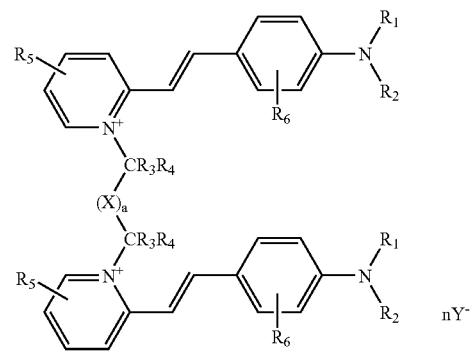

wherein:

$R_1$ and $R_2$, which may be identical or different, are chosen from:
hydrogen atoms;
linear and branched alkyl radicals comprising 1 to 10 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
aryl and arylalkyl radicals, wherein the aryl groups comprising 6 carbon atoms and the alkyl groups comprise 1 to 4 carbon atoms; the aryl groups optionally be substituted with at least one linear or branched alkyl radicals comprising 1 to 4 carbon atoms optionally interrupted with at least one entity chosen from hetero atoms and groups comprising at least one hetero atom and optionally substituted with at least entity chosen from one hetero atoms, groups comprising at least one hetero atom, and halogen atoms;
$R_1$ and $R_2$ is optionally linked so as to form a heterocycle with the nitrogen atom and optionally further comprises at least one hetero atom, wherein the heterocycle is optionally substituted with at least one entity chosen from linear and branched alkyl radicals optionally interrupted with at least one entity chosen from hetero atoms and groups comprising at least one hetero atom and optionally substituted with at least one entity chosen from hetero atoms, groups comprising at least one hetero atom, and halogen atoms;
$R_1$ or $R_2$ is also optionally included in a heterocycle comprising the nitrogen atom and one of the carbon atoms of the phenyl group comprising the nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms and linear and branched alkyl radicals comprising 1 to 4 carbon atoms, optionally interrupted with at least one hetero atom;

$R_6$, which may be identical or different, is chosen from hydrogen atoms; halogen atoms; and linear and branched alkyl radicals comprising 1 to 4 carbon atoms, optionally substituted with at least one entity chosen from hetero atoms, groups comprising at least one hetero atom and halogen atoms, and interrupted with at least one entity chosen from hetero atoms and groups comprising at least one hetero atom;

X is chosen from:
- linear and branched alkyl radicals comprising 1 to 14 carbon atoms and alkenyl radicals comprising 2 to 14 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
- 5- and 6-membered heterocyclic radicals optionally substituted with at least one entity chosen from linear and branched alkyl radicals comprising 1 to 14 carbon atoms, optionally substituted with at least one hetero atom; linear and branched aminoalkyl radicals comprising 1 to 4 carbon atoms, optionally substituted with at least one hetero atom; and halogen atoms;
- fused and non-fused aromatic and diaromatic radicals, optionally separated with an alkyl radical comprising 1 to 4 carbon atoms, wherein the aromatic and diaromatic radicals are optionally substituted with at least one entity chosen from halogen atoms, and alkyl radicals comprising 1 to 10 carbon atoms optionally substituted and/or interrupted with at least one hetero atom and/or group comprising at least one hetero atom;
- dicarbonyl radicals;
- the group X optionally comprising at least one cationic charge;

a is equal to 0 or 1;

$Y^-$, which may be identical or different, is chosen from organic and mineral anions; and n is an integer ranging from 2 to the number of cationic charges present in the fluorescent dye;

with the exception of the dye for which:
X is chosen from unsubstituted linear alkyl radicals comprising 1 or 4 carbon atoms wherein a is equal to 1 or a is equal to 0; and $R_1$ and $R_2$ simultaneously are methyl radicals; $R_5$ and $R_6$ are hydrogen atoms; $R_3$ and $R_4$, which may be identical, are hydrogen atoms;

X is chosen from ethyl, linear and branched unsubstituted $C_3$ alkyl radicals, wherein a is equal to 1; $R_3$ and $R_4$, which are identical, are hydrogen atoms; $R_5$ is a hydrogen atom; wherein $R_1$ and $R_2$:
- are identical, and are methyl radicals and, $R_6$ is chosen from a hydrogen atom and a methyl radical in an ortho position relative to the carbon atom of the benzene ring bearing the carbon-carbon unsaturated bond; and
- are identical, are ethyl radicals, and $R_6$ is chosen from hydrogen atoms and methoxy radicals in an ortho position relative to the carbon atom of the benzene ring bearing the carbon-carbon unsaturated bond; or
- are different, and are chosen from ethyl radicals and ethyl radicals substituted with an entity chosen from dimethylamino, trimethylammonium and benzyldimethylammonium groups;

X is chosen from phenyl radicals linked to the groups $CR_3R_4$ via bonds in the 1,4 position relative to each other; $R_3$ and $R_4$, which are identical, are hydrogen atoms; wherein a is equal to 1; $R_5$ is a hydrogen atom; wherein $R_1$ and $R_2$:
- are identical, and are methyl radicals, $R_6$ is chosen from hydrogen atoms and methyl radicals in an ortho position relative to the carbon atom of the benzene ring bearing the carbon-carbon unsaturated bond;
- and are identical, comprise ethyl radicals, and $R_6$ is chosen from hydrogen atoms and methoxy radicals in an ortho position relative to the carbon atom of the benzene ring bearing the carbon-carbon unsaturated bond; or
- are different, and are chosen from ethyl radicals and ethyl radicals substituted with an entity chosen from dimethylamino, trimethylammonium and benzyldimethylammonium groups; and optionally at least one entity chosen from direct dyes, oxidation bases, and couplers; and a second compartment comprising at least one oxidizing agent.

* * * * *

UNITED STATES PATENT AND TRADEMARK OFFICE
CERTIFICATE OF CORRECTION

PATENT NO. : 7,303,589 B2
APPLICATION NO. : 10/814336
DATED : December 4, 2007
INVENTOR(S) : Andrew Greaves et al.

It is certified that error appears in the above-identified patent and that said Letters Patent is hereby corrected as shown below:

Col. 33, line 45, "non-fluorsecent" should read --non-fluorescent--.

Col. 38, line 1, "alklene" should read --alkene--.

Col. 38, line 27, "isoptionally" should read --is optionally--.

Col. 38, line 32, "linear branched" should read --linear or branched--.

Col. 39, lines 10-11, "at least one—C(=O)O—" should read
--at least one —C(=O)O—;--.

Col. 40, line 53, "ito 10" should read --1 to 10--.

Col. 40, lines 62-63, "aryl groups optionally be substituted" should read --aryl groups may optionally be substituted--.

Col. 41, line 1, "from one hetero atoms" should read --from hetero atoms--.

Col. 41, line 48, "hetero atom" should read --hetero atom;--.

Col. 42, line 44, "hetero atom" should read --hetero atom;--.

Col. 45, lines 14-15, "aryl groups optionally be substituted" should read --aryl groups may optionally be substituted--.

Col. 45, line 20, "from one hetero atoms" should read --from hetero atoms--.

Col. 48, line 1, "isoptionally" should read --is optionally--.

Col. 48, line 6, "linear branched" should read --linear or branched--.

Col. 48, line 52, "at least one—C(=O)O—" should read
--at least one —C(=O)O—;--.

Col. 50, lines 35-36, "aryl groups optionally be substituted" should read --aryl groups may optionally be substituted--.

UNITED STATES PATENT AND TRADEMARK OFFICE
CERTIFICATE OF CORRECTION

PATENT NO.         : 7,303,589 B2
APPLICATION NO.    : 10/814336
DATED              : December 4, 2007
INVENTOR(S)        : Andrew Greaves et al.

It is certified that error appears in the above-identified patent and that said Letters Patent is hereby corrected as shown below:

Col. 50, line 41, "from one hetero atoms" should read --from hetero atoms--.

Signed and Sealed this

Sixth Day of May, 2008

JON W. DUDAS
*Director of the United States Patent and Trademark Office*